(12) United States Patent
Xu et al.

(10) Patent No.: US 12,269,794 B2
(45) Date of Patent: Apr. 8, 2025

(54) FLUIDIZED CATALYTIC CONVERSION METHOD FOR MAXIMIZING PRODUCTION OF PROPYLENE

(71) Applicants: CHINA PETROLEUM & CHEMICAL CORPORATION, Beijing (CN); SINOPEC RESEARCH INSTITUTE OF PETROLEUM PROCESSING CO., LTD., Beijing (CN)

(72) Inventors: Youhao Xu, Beijing (CN); Yanfen Zuo, Beijing (CN); Xingtian Shu, Beijing (CN); Xieqing Wang, Beijing (CN); Yibin Luo, Beijing (CN); Yunpeng Zhang, Beijing (CN); Yueyang Han, Beijing (CN); Lingyin Du, Beijing (CN)

(73) Assignees: CHINA PETROLEUM & CHEMICAL CORPORATION, Beijing (CN); SINOPEC RESEARCH INSTITUTE OF PETROLEUM PROCESSING CO., LTD., Beijing (CN)

(*) Notice: Subject to any disclaimer, the term of this patent is extended or adjusted under 35 U.S.C. 154(b) by 38 days.

(21) Appl. No.: 18/260,845

(22) PCT Filed: Jun. 24, 2021

(86) PCT No.: PCT/CN2021/101926
§ 371 (c)(1),
(2) Date: Jul. 10, 2023

(87) PCT Pub. No.: WO2022/147971
PCT Pub. Date: Jul. 14, 2022

(65) Prior Publication Data
US 2024/0076250 A1    Mar. 7, 2024

(30) Foreign Application Priority Data

Jan. 11, 2021 (CN) .......................... 202110032113.X
Mar. 19, 2021 (CN) .......................... 202110296904.3

(51) Int. Cl.
*C07C 4/06* (2006.01)
*C07C 7/04* (2006.01)

(52) U.S. Cl.
CPC .................. *C07C 4/06* (2013.01); *C07C 7/04* (2013.01); *C07C 2521/04* (2013.01); *C07C 2523/04* (2013.01)

(58) Field of Classification Search
None
See application file for complete search history.

(56) References Cited

U.S. PATENT DOCUMENTS 9,101,853 B2 * 8/2015 Koseoglu ................ C10G 11/18
9,550,708 B2 * 1/2017 Mandal ................ C10G 11/182
(Continued)

FOREIGN PATENT DOCUMENTS

CN         101092323 A       12/2007
CN         101239878 A        8/2008
(Continued)

*Primary Examiner* — Ali Z Fadhel
(74) *Attorney, Agent, or Firm* — NKL Law; Allen Xue

(57) ABSTRACT

A fluidized catalytic conversion method for maximizing the production of propylene includes the steps of: 1) contacting a heavy feedstock oil with a catalytic conversion catalyst having a temperature of 650° C. or higher for reaction; 2) contacting a hydrocarbon oil feedstock having an olefin content of 50 wt % or more with the catalytic conversion catalyst after the reaction of step 1); 3) separating a first catalytic cracking distillate oil and a second catalytic cracking distillate oil from the resulting reaction products; 4) separating an olefin-rich stream from the first catalytic cracking distillate oil; and 5) recycling the olefin-rich
(Continued)

stream. The method can effectively improve the yield of propylene and realize an effective utilization of petroleum resources.

18 Claims, 3 Drawing Sheets

(56) References Cited

U.S. PATENT DOCUMENTS

| | | | |
|---|---|---|---|
| 2005/0087478 A1 | 4/2005 | Zones et al. | |
| 2010/0158767 A1 | 6/2010 | Mehlberg et al. | |
| 2010/0240937 A1* | 9/2010 | Gartside | C07C 4/06 585/315 |
| 2013/0001129 A1* | 1/2013 | Xu | C10G 45/12 208/68 |
| 2013/0056393 A1* | 3/2013 | Subramani | B01J 35/51 502/67 |
| 2017/0107430 A1* | 4/2017 | Koseoglu | C10G 51/026 |
| 2020/0291306 A1* | 9/2020 | Aitani | B01J 29/80 |
| 2023/0159411 A1* | 5/2023 | Yao | C07C 7/005 585/324 |
| 2023/0407190 A1* | 12/2023 | Narayanaswamy | C10G 47/16 |

FOREIGN PATENT DOCUMENTS

| | | |
|---|---|---|
| CN | 101760228 A | 6/2010 |
| CN | 104334691 A | 2/2015 |
| CN | 106609147 A | 5/2017 |
| CN | 109704903 A | 5/2019 |
| CN | 109704904 A | 5/2019 |
| JP | 2005520885 A5 | 4/2006 |
| JP | 2007527937 A | 10/2007 |
| JP | 2015512969 A | 4/2015 |
| TW | 201217511 A | 5/2012 |
| TW | 202100497 A | 1/2021 |
| WO | 2020192490 A1 | 10/2020 |

* cited by examiner

FLUIDIZED CATALYTIC CONVERSION METHOD FOR MAXIMIZING PRODUCTION OF PROPYLENE

CROSS REFERENCE TO RELATED APPLICATIONS

This application is a U.S. national stage entry of PCT international application no. PCT/CN2021/101926, filed on Jun. 24, 2021, which claims priority from Chinese patent application No. 202110032113.X, titled "a catalytic conversion method for maximizing production of propylene", filed on Jan. 11, 2021 and from Chinese patent application No. 202110296904.3, titled "a catalytic conversion method for maximizing production of propylene", filed on Mar. 19, 2021, the content of each is incorporated herein by reference in its entirety.

TECHNICAL FIELD

The present application relates to the field of fluidized catalytic conversion, particularly to a fluidized catalytic conversion method for maximizing production of propylene.

BACKGROUND ART

Petrochemical industry is an important pillar industry, provides a large amount of chemical raw materials for industry, agriculture, traffic, national defense and the like, and propylene and ethylene are two most important basic raw materials for modern petrochemical industry. However, with the increasing production of oil fields, the available yield of conventional crude oil is gradually reduced, the quality of crude oil is becoming poor, and the crude oil tends to be deteriorated and heavy. Propylene is an important organic chemical raw material, and is mainly used for preparing acrylonitrile, propylene oxide, acetone and the like. Ethylene and propylene are increasingly used as important chemical intermediates for preparing various important organic chemical raw materials, synthetic resins, synthetic rubbers, various fine chemicals, and the like.

The traditional route for preparing ethylene and propylene by steam cracking has a large demand for light hydrocarbons such as naphtha and the like, the existing crude oil is normally heavy, and light chemical oil is difficult to meet the demand of ethylene and propylene raw materials. Research institutions expect that the global annual average growth rate of gasoline pool will be less than 1% from 2018 to 2026, but propylene will increase by about 4%. Appropriage use of high-carbon olefins in refinery process to prepare ethylene and propylene by cracking can meet the goal of quality improvement and efficiency improvement of petrochemical enterprises, and the time requirement of energy transformation.

CN 101092323A discloses a method for preparing ethylene and propylene from a mixture of C4-C8 olefins, comprising reacting the mixture at a reaction temperature of 400-600° C. and an absolute pressure of 0.02-0.3 MPa, and recycling 30-90 wt % of a C4 fraction to the reactor after separating in a separator for further cracking. The method improves the conversion rate of olefin mainly by recycling the C4 fraction, the ethylene and propylene obtained account for not less than 62% of the total amount of the olefin feedstock, but it suffers from the problems including a relatively low ethylene/propylene ratio, which cannot be flexibly adjusted according to market demands, low reaction selectivity, high butylene content in the product, and energy consumption for C4 separation.

CN 101239878A discloses a method using a mixture rich in C4+ olefins as a raw material, comprising reacting at a reaction temperature of 400-680° C., a reaction pressure of −0.09 MPa to 1.0 MPa and a weight space velocity of 0.1 to 50 $h^{-1}$, the resulting product has an ethylene/propylene ratio of lower than 0.41, and as the temperature rises, the ethylene/propylene ratio increases, and the production of hydrogen, methane and ethane increases.

Therefore, there is a need in the art for a novel fluidized catalytic conversion method to increase the production of ethylene and propylene and improve the selectivity of ethylene and propylene.

SUMMARY OF THE INVENTION

It is an object of the present application to provide a method for maximizing the production of propylene from a hydrocarbon-containing feedstock, which is effective in increasing the yield of propylene while also having a high yield of ethylene, a high selectivity and a low yield of dry gas.

To achieve the above object, the present application provides a fluidized catalytic conversion method for maximizing the production of propylene, comprising the steps of:

1) introducing a heavy feedstock oil into a first reaction zone of a fluidized catalytic conversion reactor, contacting with a catalytic conversion catalyst having a temperature of 650° C. or higher, and reacting under first catalytic conversion reaction conditions;
2) introducing a hydrocarbon oil feedstock having an olefin content of 50 wt % or more into a second reaction zone of the fluidized catalytic conversion reactor downstream of the first reaction zone, contacting with the catalytic conversion catalyst from the first reaction zone after the reaction of step 1), and reacting under second catalytic conversion conditions;
3) separating the effluent of the fluidized catalytic conversion reactor to obtain reaction products and a spent catalyst, and carrying out a first separation on the reaction products to obtain ethylene, propylene, butylene, a first catalytic cracking distillate oil and a second catalytic cracking distillate oil; the initial boiling point of the first catalytic cracking distillate oil is more than 20° C., the final boiling point of the second catalytic cracking distillate oil is less than 550° C., and the cut point between the first catalytic cracking distillate oil and the second catalytic cracking distillate oil is within a range of 140° C. and 250° C.;
4) carrying out a second separation on the first catalytic cracking distillate oil to obtain an olefin-rich stream having a C5+ olefin content of at least 50 wt %;
5) recycling at least a part of the olefin-rich stream to step 2) for further reaction; and
6) recycling at least a part of the butylene separated in step 3) to the fluidized catalytic conversion reactor upstream of the position at which the heavy feedstock oil is introduced to contact with the catalytic conversion catalyst for reaction under third catalytic conversion conditions, wherein the first catalytic conversion conditions include: a reaction temperature of 500-800° C., a reaction pressure of 0.05-1 MPa, a reaction time of 0.01-100 seconds, and a weight ratio of the catalytic conversion catalyst to the heavy feedstock oil of (1-200):1; and the second catalytic conversion conditions include: a reaction temperature of 400-680° C., a reaction pressure of 0.05-1 MPa, a reaction time of 0.01-100 seconds, and a weight ratio of the catalytic conversion catalyst to the hydrocarbon oil feedstock of (1-100):1.

the third catalytic conversion conditions include: a reaction temperature of 650-800° C., a reaction pressure of 0.05-1 MPa, a reaction time of 0.01-10 seconds, and a weight ratio of the catalytic conversion catalyst to the butylene of (20-200):1.

preferably, the method further comprises the steps of:

2a) introducing an oxygen-containing organic compound into the second reaction zone of the fluidized catalytic conversion reactor to contact with the catalytic conversion catalyst therein for reaction under fourth catalytic conversion conditions including:

a reaction temperature of 300-550° C.,
a reaction pressure of 0.05-1 MPa,
a reaction time of 0.01-100 seconds,
a weight ratio of the catalytic conversion catalyst to the oxygen-containing organic compound feedstock of (1-100):1.

Preferably, the method further comprises the steps of:

7) carrying out a hydrotreatment on the second catalytic cracking distillate oil to obtain a hydrogenated catalytic cracking distillate oil, and recycling the hydrogenated catalytic cracking distillate oil to the first reaction zone of the fluidized catalytic conversion reactor for further reaction.

In the fluidized catalytic conversion method of the present application, the heavy feedstock oil and the olefin-rich hydrocarbon oil feedstock are subjected to high-temperature cracking respectively, the butylene and the olefin-rich stream in the separated product are recycled to the reactor for further reaction, and meanwhile, the catalytic gas oil with high boiling point in the separated product may be subjected to hydrotreatment and then to further reaction. By refining low-added-value olefins produced in chemical processes by a specific route, the yield of propylene may be effectively increased, an effective utilization of petroleum resources may be realized, the traditional scheme of producing propylene by steam cracking with high energy consumption may be replaced, and meanwhile, the method according to the present application also has the advantages of high ethylene yield, high selectivity and low dry gas yield.

Other characteristics and advantages of the present application will be described in detail in the detailed description hereinbelow.

BRIEF DESCRIPTION OF THE DRAWINGS

The drawings, forming a part of the present description, are provided to help the understanding of the present application, and should not be considered to be limiting. The present application may be interpreted with reference to the drawings in combination with the detailed description hereinbelow. In the drawings.

Figure 1:
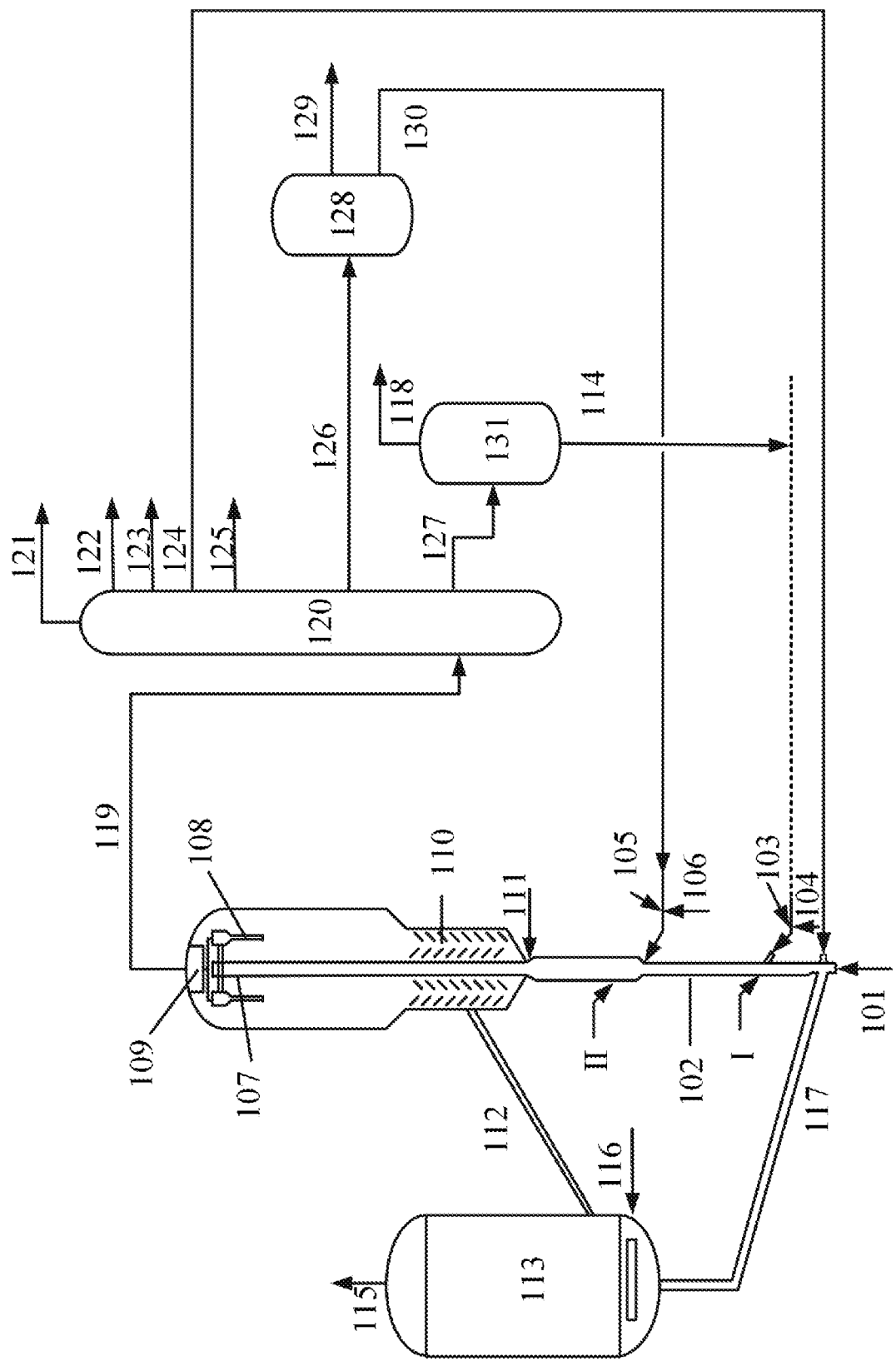
FIG. 1 shows a schematic flow diagram of a preferred embodiment of the fluidized catalytic conversion method of the present application.

| Description of the reference numerals | | |
|---|---|---|
| I first reaction zone | II second reaction zone | III third reaction zone |
| 101 pipeline | 102 fluidized catalytic conversion reactor | 103 pipeline |
| 104 pipeline | 105 pipeline | 106 pipeline |
| 107 outlet section | 108 cyclone separator | 109 plenum chamber |
| 110 stripping section | 111 pipeline | 112 standpipe |
| 113 regenerator | 114 pipeline | 115 pipeline |
| 116 pipeline | 117 pipeline | 118 pipeline |
| 119 reactor vapor line | 120 product fractionator | 121 pipeline |
| 122 pipeline | 123 pipeline | 124 pipeline |
| 125 pipeline | 126 pipeline | 127 pipeline |
| 128 olefin separator | 129 pipeline | 130 pipeline |
| 131 hydrotreator | | |
| 201 pipeline | 202 fluidized catalytic conversion reactor | 203 pipeline |
| 204 pipeline | 205 pipeline | 206 pipeline |
| 207 outlet section | 208 cyclone separator | 209 plenum chamber |
| 210 stripping section | 211 pipeline | 212 standpipe |
| 213 regenerator | 214 pipeline | 215 pipeline |
| 216 pipeline | 217 pipeline | 218 pipeline |
| 219 reactor vapor line | 220 product fractionator | 221 pipeline |
| 222 pipeline | 223 pipeline | 224 pipeline |
| 225 pipeline | 226 pipeline | 227 pipeline |
| 228 olefin separator | 229 pipeline | 230 pipeline |
| 231 pipeline | 232 hydrotreator | |
| 301 pipeline | 302 fluidized catalytic conversion reactor | 303 pipeline |
| 304 pipeline | 305 pipeline | 306 pipeline |
| 307 pipeline | 308 outlet section | 309 cyclone separator |
| 310 plenum chamber | 311 stripping section | 312 pipeline |
| 313 standpipe | 314 regenerator | 315 pipeline |
| 316 pipeline | 317 pipeline | 318 pipeline |
| 319 reactor vapor line | 320 product fractionator | 321 pipeline |
| 322 pipeline | 323 pipeline | 324 pipeline |
| 325 pipeline | 326 pipeline | 327 pipeline |
| 328 pipeline | 329 olefin separator | 330 pipeline |
| 331 pipeline | 332 hydrotreater | 333 pipeline |

DETAILED DESCRIPTION OF THE INVENTION

The present application will be further described hereinafter in detail with reference to the drawing and specific embodiments thereof. It should be noted that the specific embodiments of the present application are provided for illustration purpose only, and are not intended to be limiting in any manner.

Any specific numerical value, including the endpoints of a numerical range, described in the context of the present application is not restricted to the exact value thereof, but should be interpreted to further encompass all values close to said exact value, for example all values within ±5% of said exact value. Moreover, regarding any numerical range described herein, arbitrary combinations can be made between the endpoints of the range, between each endpoint and any specific value within the range, or between any two specific values within the range, to provide one or more new numerical range(s), where said new numerical range(s) should also be deemed to have been specifically described in the present application.

Unless otherwise stated, the terms used herein have the same meaning as commonly understood by those skilled in the art; and if the terms are defined herein and their definitions are different from the ordinary understanding in the art, the definition provided herein shall prevail.

In the present application, the term "C4+" means having at least 4 carbon atoms, for example the term "C4+ olefins" refers to olefins having at least 4 carbon atoms, while the term "C4+ fraction" refers to a fraction of which the compounds have at least 4 carbon atoms. Correspondingly, the term "C5+" means having at least 5 carbon atoms.

In the context of the present application, in addition to those matters explicitly stated, any matter or matters not mentioned are considered to be the same as those known in the art without any change. Moreover, any of the embodiments described herein can be freely combined with another one or more embodiments described herein, and the technical solutions or ideas thus obtained are considered as part of the original disclosure or original description of the present application, and should not be considered to be a new matter that has not been disclosed or anticipated herein, unless it is clear to the person skilled in the art that such a combination is obviously unreasonable.

All of the patent and non-patent documents cited herein, including but not limited to textbooks and journal articles, are hereby incorporated by reference in their entirety.

As stated above, the present application provides a fluidized catalytic conversion method for maximizing the production of propylene, comprising the steps of:

1) introducing a heavy feedstock oil into a first reaction zone of a fluidized catalytic conversion reactor to contact with a catalytic conversion catalyst having a temperature of 650° C. or higher for reaction;
2) introducing a hydrocarbon oil feedstock having an olefin content of 50 wt % or more into a second reaction zone of the fluidized catalytic conversion reactor downstream of the first reaction zone, to contact with the catalytic conversion catalyst from the first reaction zone after the reaction of step 1) for reaction;
3) separating the effluent of the fluidized catalytic conversion reactor to obtain reaction products and a spent catalyst, and carrying out a first separation on the reaction products to obtain ethylene, propylene, butylene, a first catalytic cracking distillate oil and a second catalytic cracking distillate oil; the initial boiling point of the first catalytic cracking distillate oil is more than 20° C., the final boiling point of the second catalytic cracking distillate oil is less than 550° C., and the cut point between the first catalytic cracking distillate oil and the second catalytic cracking distillate oil is within a range of 140° C. and 250° C.;
4) carrying out a second separation on the first catalytic cracking distillate oil to obtain an olefin-rich stream having a C5+ olefin content of at least 50 wt %;
5) recycling at least a part of the olefin-rich stream to step 2) for further reaction; and
6) recycling at least a part of the butylene separated in step 3) to the fluidized catalytic conversion reactor upstream of the position at which the heavy feedstock oil is introduced to contact with the catalytic conversion catalyst for reaction.

In a preferred embodiment, the reaction of step 1) is carried out under first catalytic conversion conditions, which may include: a reaction temperature of 500-800° C., a reaction pressure of 0.05-1 MPa, a reaction time of 0.01-100 seconds, and a weight ratio of the catalytic conversion catalyst to the heavy feedstock oil of (1-200):1; the reaction of step 2) is carried out under second catalytic conversion conditions, which may include: a reaction temperature of 400-680° C., a reaction pressure of 0.05-1 MPa, a reaction time of 0.01-100 seconds, and a weight ratio of the catalytic conversion catalyst to the hydrocarbon oil feedstock of (1-100):1.

In a further preferred embodiment, the first catalytic conversion conditions may include: a reaction temperature of 510-780° C., a reaction pressure of 0.1-0.8 MPa, a reaction time of 0.1-80 seconds, and a weight ratio of the catalytic conversion catalyst to the heavy feedstock oil of (3-180):1; the second catalytic conversion conditions may include: a reaction temperature of 450-650° C., a reaction pressure of 0.1-0.8 MPa, a reaction time of 0.1-80 seconds, and a weight ratio of the catalytic conversion catalyst to the hydrocarbon oil feedstock of (3-70):1.

According to the present application, the heavy feedstock oil used in step 1) may be those commonly used in the art, and is not strictly limited herein. For example, the heavy feedstock oil may be a petroleum hydrocarbon and/or a mineral oil; the petroleum hydrocarbon may be selected from the group consisting of vacuum gas oil, atmospheric gas oil, coking gas oil, deasphalted oil, vacuum residuum, atmospheric residuum, and heavy aromatic raffinate, or combinations thereof; the mineral oil may be selected from coal liquefaction oil, oil sand oil and shale oil, or a combination thereof.

In a preferred embodiment, the hydrocarbon oil feedstock used in step 2) may have an olefin content of 80 wt % or more, preferably 90 wt % or more; more preferably, the hydrocarbon oil feedstock may be a pure olefin feedstock.

According to the present application, the hydrocarbon oil feedstock may be derived from a variety of sources, and there is no particular limitation herein. In some embodiments, the olefins in the hydrocarbon oil feedstock may be derived from a C4+ fraction produced by dehydrogenation of an alkane feedstock, a C4+ fraction produced by a catalytic cracking unit in an oil refinery, a C4+ fraction produced by a steam cracking unit in an ethylene plant, a C4+ olefin-rich byproduct fraction of an MTO process, and a C4+ olefin-rich byproduct fraction of an MTP process. In a preferred embodiment, the alkane feedstock for dehydrogenation may be selected from naphtha, aromatic raffinate, light hydrocarbons, or combinations thereof.

According to the present application, the dehydrogenation of the alkane feedstock may be carried out by contacting the alkane feedstock with a dehydrogenation catalyst, wherein the dehydrogenation conditions used may include: an inlet temperature of the reactor of 400-700° C., a volume space velocity of alkane of 200-5000 $h^{-1}$, and a reaction pressure of 0-1.0 MPa.

Preferably, the dehydrogenation catalyst consists of a carrier and an active component and a promoter supported on the carrier; the carrier may be present in an amount of 60 to 90 wt %, the active component may be present in an amount of 8 to 35 wt %, and the promoter may be present in an amount of 0.1 to 5 wt %, based on the total weight of the dehydrogenation catalyst.

Further preferably, the carrier may be an alumina comprising a modifier; wherein, based on the total weight of the dehydrogenation catalyst, the modifier may be present in an amount of 0.1-2 wt %, and the modifier may be La and/or Ce; the active component may be platinum and/or chromium; the promoter may be a composition of bismuth and an alkali metal component or a composition of bismuth and an alkaline earth metal component, wherein the molar ratio of bismuth to the active component is 1:(5-50); the molar ratio of bismuth to the alkali metal component is 1:(0.1-5); the molar ratio of bismuth to the alkaline earth metal component is 1:(0.1-5). Particularly preferably, the alkali metal component may be one or more selected from Li, Na and K; the alkaline earth metal component may be one or more selected from Mg, Ca and Ba.

According to the present application, the butylene introduced into the fluidized catalytic conversion reactor for further reaction is contacted with the hot catalytic conversion catalyst before the heavy feedstock oil. As the difficulty of cracking the hydrocarbons is increased along with the reduction of number of carbon atoms, and the energy required for cracking the butylene is relatively high, the butylene is the first to contact with the high-temperature catalytic conversion catalyst, so that the butylene conversion rate and the selectivity of ethylene and propylene products may be improved, the generation of byproducts caused by co-feeding of the butylene and heavy feedstock oil may be avoided, and a high-efficiency utilization of resources may be realized.

In a preferred embodiment, the reaction of step 6) is carried out under third catalytic conversion conditions, which may include: a reaction temperature of 650-800° C., a reaction pressure of 0.05-1 MPa, a reaction time of 0.01-10 seconds, and a weight ratio of the catalytic conversion catalyst to the butylene of (20-200):1. Further preferably, the third catalytic conversion conditions include: a reaction temperature of 680-780° C., a reaction pressure of 0.1-0.8 MPa, a reaction time of 0.05-8 seconds, and a weight ratio of the catalytic conversion catalyst to the butylene of (30-180):1.

In some preferred embodiments, the fluidized catalytic conversion method of the present application further comprises the steps of: 2a) introducing an oxygen-containing organic compound into the second reaction zone of the fluidized catalytic conversion reactor to contact with the catalytic conversion catalyst for reaction therein.

Preferably, the reaction of step 2a) is carried out under fourth catalytic conversion conditions, which may include: a reaction temperature of 300-550° C., a reaction pressure of 0.05-1 MPa, a reaction time of 0.01-100 seconds, and a weight ratio of the catalytic conversion catalyst to the oxygen-containing organic compound feedstock of (1-100):1. Further preferably, the fourth catalytic conversion conditions include: a reaction temperature of 400-530° C., a reaction pressure of 0.1-0.8 MPa, a reaction time of 0.1-80 seconds, and a weight ratio of the catalytic conversion catalyst to the oxygen-containing organic compound feedstock of (3-80) 1.

In such preferred embodiments of the present application, the oxygen-containing organic compound may be fed alone or in admixture with other feedstocks. For example, the oxygen-containing organic compound may be mixed with the hydrocarbon oil feedstock and then fed to the second reaction zone of the fluidized catalytic conversion reactor, or the oxygen-containing organic compound may be fed to the second reaction zone of the fluidized catalytic conversion reactor downstream of the position at which the hydrocarbon oil feedstock is introduced.

Particularly preferably, the oxygen-containing organic compound comprises at least one of methanol, ethanol, dimethyl ether, methyl ethyl ether and ethyl ether. For example, the oxygen-containing organic compound, such as methanol or dimethyl ether, may be derived from coal-based or natural gas-based syngas.

In some preferred embodiments, the fluidized catalytic conversion method of the present application further comprises the steps of: 7) carrying out a hydrotreatment on the second catalytic cracking distillate oil obtained in step 3) to obtain a hydrogenated catalytic cracking distillate oil, and recycling the hydrogenated catalytic cracking distillate oil to the first reaction zone of the fluidized catalytic conversion reactor for further reaction. In this embodiment, the second catalytic cracking distillate oil is subjected to hydrotreatment and then to further reaction, so that the side reaction of generating small molecular alkane and coke may be further reduced, the yield of ethylene and propylene can be improved, and the effective utilization of carbon atoms can be realized.

Preferably, the hydrotreatment conditions may include: a hydrogen partial pressure of 3.0-20.0 MPa, a reaction temperature of 300-450° C., a hydrogen-to-oil volume ratio of 300-2000, and a volume space velocity of 0.1-3.0 $h^{-1}$.

According to the present application, the hydrogenation catalyst used in step 7) may be those commonly used in the art, and there is no particular limitation herein. For example, the hydrogenation catalyst may comprise a carrier and a metal component and optionally an additive supported on the carrier. preferably, the hydrogenation catalyst comprises 20 to 90 wt % of a carrier, 10 to 80 wt % of a supported metal, and 0 to 10 wt % of an additive, based on the total weight of the hydrogenation catalyst. Further preferably, the carrier is alumina and/or amorphous silica-alumina, the metal component is a Group VIB metal and/or a Group VIII metal, and the additive is at least one selected from fluorine, phosphorus, titanium and platinum; still more preferably, the Group VIB metal is Mo or/and W and the Group VIII metal is Co or/and Ni. Particularly preferably, the additive is present in an amount of from 0 to 10 wt %, the Group VIB metal is present in an amount of from 12 to 39 wt % and the Group VIII metal is present in an amount of from 1 to 9 wt %, based on the total weight of the hydrogenation catalyst.

In a preferred embodiment, the fluidized catalytic conversion method of the present application further comprises the steps of: 8) regenerating the spent catalyst obtained by the separation in step 3) by coke burning to obtain a regenerated catalyst having a temperature of 650° C. or higher, and then recycling the regenerated catalyst to the upstream of the first reaction zone of the fluidized catalytic conversion reactor for use as the catalytic conversion catalyst.

In a preferred embodiment, the catalytic conversion catalyst used herein may comprise from 1 to 50 wt % of a molecular sieve, from 5 to 99 wt % of an inorganic oxide, and from 0 to 70 wt % of a clay, based on the weight of the catalyst.

In a further preferred embodiment, in the catalytic conversion catalyst, the molecular sieve serves as an active component, and the molecular sieve may comprise at least one of a macroporous molecular sieve, a mesoporous molecular sieve, and a microporous molecular sieve.

In some still further preferred embodiments, the mesoporous molecular sieve may be a ZSM molecular sieve, for example, the ZSM molecular sieve may be at least one selected from the group consisting of ZSM-5, ZSM-11, ZSM-12, ZSM-23, ZSM-35, and ZSM-48; the microporous molecular sieve may be a SAPO molecular sieve and/or an SSZ molecular sieve, for example, the SAPO molecular sieve may be at least one selected from the group consisting of SAPO-34, SAPO-11 and SAPO-47, and the SSZ molecular sieve may be at least one selected from the group consisting of SSZ-13, SSZ-39 and SSZ-62; the macroporous molecular sieve may be selected from REY molecular sieves, REHY molecular sieves, ultrastable Y molecular sieves, high-silica Y molecular sieves, Beta molecular sieves and other molecular sieves of similar structure, or mixtures thereof.

In a particularly preferred embodiment, the molecular sieve comprises from 40 wt % to 100 wt %, preferably from 50 wt % to 100 wt %, of the mesoporous molecular sieve, and from 0 wt % to 30 wt %, preferably from 0 wt % to 25 wt %, of the microporous molecular sieve, and from 0 wt % to 30 wt %, preferably from 0 wt % to 25 wt %, of the macroporous molecular sieve, based on the total weight of the molecular sieve.

In a further preferred embodiment, in the catalytic conversion catalyst, the inorganic oxide serves as a binder, and preferably, the inorganic oxide may be selected from silica ($SiO_2$) and/or alumina ($Al_2O_3$).

In a further preferred embodiment, in the catalytic conversion catalyst, the clay serves as a matrix, preferably the clay may be selected from kaolin and/or halloysite.

In a further preferred embodiment, the catalytic conversion catalyst may also comprise a modifying element to further improve the performance of the catalytic conversion catalyst. The modifying element may be at least one selected from a non-metal element, a transition metal element, and a rare earth metal element; still more preferably, the non-metallic element may be phosphorus, the transition metal element may be selected from iron, cobalt and nickel, and the content of the modifying element is 0.1-3 wt % of the catalytic conversion catalyst.

In a preferred embodiment, the olefin-rich stream separated in step 4) has an olefin content of 80 wt % or more, more preferably has a C5+ olefin content of 80 wt % or more. The higher the olefin content in the olefin-rich stream, the better the effect of refining and the better the utilization of resources.

In some preferred embodiments, the second separation of step 4) further comprises: separating from the first catalytic cracking distillate oil an olefin-depleted stream, a first olefin-rich stream having a lower boiling point and a second olefin-rich stream having a higher boiling point; the cut point between the first stream and the second stream is in a range of 140-200° C.; and, the step 5) further comprises introducing the first olefin-rich streams into the second reaction zone for further reaction; and introducing the second olefin-rich stream into a third reaction zone of the fluidized catalytic conversion reactor downstream of the second reaction zone for further reaction.

The inventors of the present application have found, after a great number of experiments, that olefins with long carbon chains have poor capability of inhibiting the formation of methane while producing propylene by cracking, as compared to olefins with short carbon chains. Taking propylene as an objective product for illustration, the longer the carbon chain of the olefin molecule subjected to catalytic cracking is, the easier the cracking is. To avoid the increase of byproducts such as methane in the product caused by cracking of the long carbon chain into small molecules at one time, olefins with long carbon chains may be cracked in a fourth reaction zone with relatively mild conditions to obtain C5-C9 olefins with short carbon chains, and the C5-C9 olefins are then recycled to the reactor for further cracking, which is beneficial to improving the yield of propylene and reducing the yield of methane. In the above preferred embodiment, the first stream and the second stream comprising C5+ olefins with different distillation ranges are respectively introduced into different reaction zones, specifically, the first stream with lower boiling point is introduced into the third reaction zone, and the second stream with higher boiling point is introduced into the fourth reaction zone, so that olefins with longer carbon chains may be prevented from being cracked into small molecules at one time, and the yield of propylene may be improved.

In a still further preferred embodiment, the conditions for further reaction of the first stream introduced into the third reaction zone may include: a reaction temperature of 600-750° C., a reaction pressure of 0.05-1 MPa, a reaction time of 0.01-100 seconds, and a weight ratio of the catalytic conversion catalyst to the first stream of (1-140):1; the conditions for further reaction of the second stream introduced into the fourth reaction zone may include: a reaction temperature of 400-650° C., a reaction pressure of 0.05-1 MPa, a reaction time of 0.01-100 seconds, and a weight ratio of the catalytic conversion catalyst to the second stream of (1-100) 1.

In a preferred embodiment, the fluidized catalytic conversion reactor may be selected from a riser reactor, which may be an equal-diameter riser reactor or a diameter-transformed riser reactor, a fluidized bed reactor, which may be a constant-linear-velocity fluidized bed reactor or an equal-diameter fluidized bed reactor, an ascending transfer line, a descending transfer line, or a combination of two or more thereof, and the diameter-transformed riser reactor may be a riser reactor as described, for example, in Chinese patent CN1078094C.

In a preferred embodiment, as shown in FIG. 1, the fluidized catalytic conversion method of the present application is carried out as follows:

A pre-lifting medium is introduced from the bottom of a fluidized catalytic conversion reactor (a riser reactor) 102 through pipeline 101, a regenerated catalytic conversion catalyst from pipeline 117 moves upwards along the fluidized catalytic conversion reactor 102 under the lifting action of the pre-lifting medium, a heavy feedstock oil is injected into the bottom of a first reaction zone I of the reactor 102 through pipeline 103 together with atomized steam from pipeline 104, where it is contacted and reacted with the hot catalyst having a temperature of 650° C. or higher and further moves upwards.

A hydrocarbon oil feedstock having an olefin content of 50 wt % or more is injected into the lower middle part of the fluidized catalytic conversion reactor 102 through pipeline 105 together with atomized steam from pipeline 106 and is mixed with the stream from the first reaction zone I in the second reaction zone II, and the hydrocarbon oil feedstock is contacted and reacted with the hot catalyst and moves upward.

The resulting reaction product and inactivated spent catalyst are passed to a cyclone separator 108 in the disengager through an outlet section 107 to conduct a separation of the spent catalyst and the reaction product, the reaction product is passed to a plenum chamber 109, and the fine catalyst powder is returned to the disengager through a dipleg. Spent catalyst in the disengager is passed to a stripping section 110 where it is contacted with stripping steam from pipeline 111. The product vapor stripped from the spent catalyst is passed to the plenum chamber 109 after passing through the cyclone separator. The stripped spent catalyst is passed to a regenerator 113 through a standpipe 112, and main air is introduced into the regenerator through pipeline 116 to burn out the coke on the spent catalyst so as to regenerate the inactivated spent catalyst. The flue gas is passed to a flue gas turbine via pipeline 115. The regenerated catalyst is passed to the reactor 102 via pipeline 117.

The reaction product (reaction product vapor) is passed to a subsequent fractionator 120 through a reactor vapor line 119, the separated hydrogen, methane and ethane are withdrawn through pipeline 121, ethylene is withdrawn through pipeline 122, propylene is withdrawn through pipeline 123, the butylene is recycled to the bottom of the reactor 102 through pipeline 124 for further reaction, propane and butane are withdrawn through pipeline 125, the first catalytic cracking distillate oil is passed into an olefin separator 128 through pipeline 126, the separated olefin-depleted stream is withdrawn through pipeline 129, the olefin-rich stream is sent to the bottom of a second reaction area II of the reactor 102 through pipeline 130 for further reaction, the second catalytic cracking distillate oil is passed into a hydrotreator 131 through pipeline 127, and a light component and a hydrogenated catalytic cracking distillate oil are obtained after a hydrotreatment, the light component is withdrawn through pipeline 118, the hydrogenated catalytic cracking distillate oil is withdrawn through pipeline 114, and optionally introduced into the first reaction zone I of the reactor 102 for further reaction.

Figure 2:
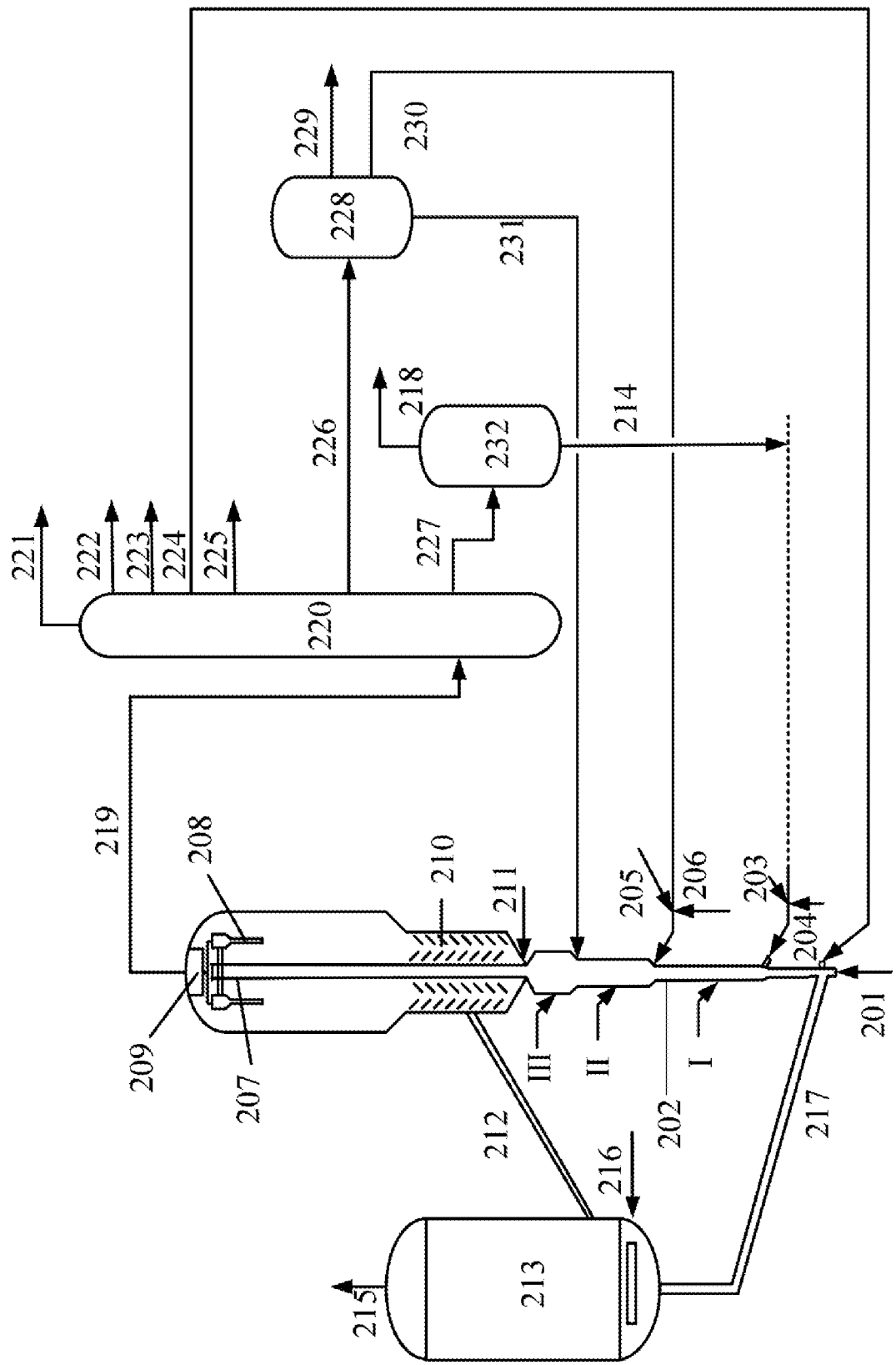
FIG. 2 shows a schematic flow diagram of another preferred embodiment of the fluidized catalytic conversion method of the present application.

FIG. 2 shows another preferred embodiment of the present application, wherein the fluidized catalytic conversion reactor is further provided with a third reaction zone downstream of the second reaction zone II, wherein the third reaction zone is appropriately enlarged for the case where the olefin-rich feedstock from external source is relatively large in amount.

As shown in FIG. 2, in this embodiment, the fluidized catalytic conversion method of the present application is carried out as follows:

A pre-lifting medium is introduced from a first reaction zone I of a fluidized catalytic conversion reactor 202 through pipeline 201, a regenerated catalytic conversion catalyst from pipeline 217 moves upwards along the reactor 202 under the lifting action of the pre-lifting medium, and a heavy feedstock oil is injected into the bottom of the first reaction zone I of the reactor 202 through pipeline 203 together with atomized steam from pipeline 204, where it is contacted and reacted with the hot catalyst having a temperature of 650° C. or higher, and moves upwards.

A hydrocarbon oil feedstock having an olefin content of 50 wt % or more is injected into the lower middle part of the fluidized catalytic conversion reactor 202 through pipeline 205 together with atomized steam from pipeline 206 and is mixed with the stream from the first reaction zone I in the second reaction zone II, and the hydrocarbon oil feedstock is contacted and reacted with the hot catalyst and moves upward.

The reaction product and deactivated spent catalyst produced in the reactor 202 are passed to a cyclone separator 208 in the disengager through an outlet section 207 to conduct a separation of the spent catalyst and the reaction product, the reaction product is passed to a plenum chamber 209, and the fine catalyst powder is returned to the disengager through a dipleg. Spent catalyst in the disengager is passed to a stripping section 210 where it is contacted with stripping steam from pipeline 211. The product vapor stripped from the spent catalyst is passed to the plenum chamber 209 after passing through the cyclone separator. The stripped spent catalyst is passed to a regenerator 213 through a standpipe 212, and main air is introduced into the regenerator through pipeline 216 to burn out the coke on the spent catalyst so as to regenerate the inactivated spent catalyst. The flue gas is passed to a flue gas turbine via pipeline 215. The regenerated catalyst is recycled to the bottom of reactor 202 via pipeline 217. The reaction product is passed to a subsequent fractionator 220 through a reactor vapor line 219, the separated hydrogen, methane and ethane are withdrawn through pipeline 221, ethylene is withdrawn through pipeline 222, propylene is withdrawn through pipeline 223, butylene is recycled to the bottom of the reactor 202 through pipeline 224 for further reaction, propane and butane are withdrawn through pipeline 225, the first catalytic cracking distillate oil is passed into an olefin separator 228 through pipeline 226, and an olefin-depleted stream, a first olefin-rich stream and a second olefin-rich stream are obtained by separation, wherein the cut point between the first stream and the second stream is within a range of 140-200° C. The olefin-depleted stream is withdrawn via pipeline 229, the first olefin-rich stream with a lower boiling point is introduced via pipeline 230 into the second reaction zone II of the reactor 202 for further reaction, and the second olefin-rich stream with a higher boiling point is introduced via pipeline 231 into the third reaction zone III of the reactor 202 for further reaction. The second catalytic cracking distillate oil is introduced into a hydrotreator 232 through pipeline 227, and a light component and a hydrogenated catalytic cracking distillate oil are obtained after a hydrotreatment, wherein the light component is withdrawn through pipeline 218, and the hydrogenated catalytic cracking distillate oil is withdrawn through pipeline 214, and optionally passed to the bottom of the first reaction zone I of the reactor 202 for further reaction.

Figure 3:
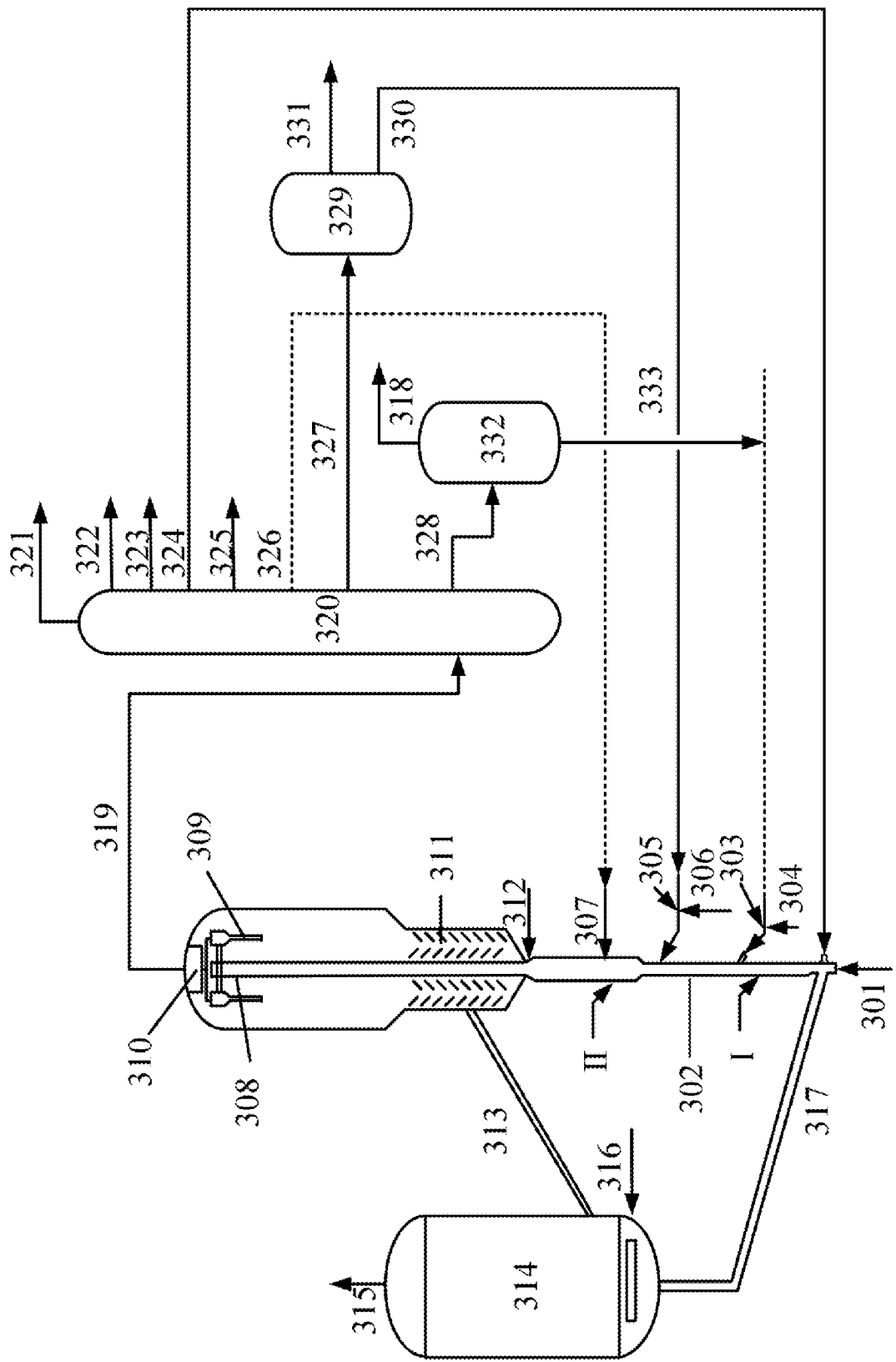
FIG. 3 shows a schematic flow diagram of yet another preferred embodiment of the fluidized catalytic conversion method of the present application.

In yet another preferred embodiment, as shown in FIG. 3, the fluidized catalytic conversion method of the present application is carried out as follows:

A pre-lifting medium is introduced from the bottom of the fluidized catalytic conversion reactor (a riser reactor) 302 through pipeline 301, a regenerated catalytic conversion catalyst from pipeline 317 moves upwards along the fluidized catalytic conversion reactor 302 under the lifting action of the pre-lifting medium, and a heavy feedstock oil is injected into the bottom of the first reaction zone I of the fluidized catalytic conversion reactor 302 through pipeline 303 together with atomized steam from pipeline 304, where it is contacted and reacted with the hot catalyst having a temperature of 650° C. or higher for reaction and further move upwards.

A hydrocarbon oil feedstock having an olefin content of greater than 50 wt % is injected via pipeline 305 into the lower middle part of the fluidized catalytic conversion reactor 302 along with atomized steam from pipeline 306 and is mixed with the stream from the first reaction zone I in the second reaction zone II, and the hydrocarbon oil feedstock is contacted and reacted with the hot catalyst and moves upward.

An oxygen-containing organic compound (e.g., methanol) is injected into the lower middle part of the second reaction zone II through pipeline 307 downstream of the position at which the hydrocarbon oil feedstock is injected, and mixed with the stream therein. The oxygen-containing organic compound is contacted and reacted with the catalyst and moves upward.

The resulting reaction product and inactivated spent catalyst are passed to a cyclone separator 309 in the disengager through an outlet section 308 to conduct a separation of the spent catalyst and the reaction product, the reaction product is passed to a plenum chamber 310, and the fine catalyst powder is returned to the disengager through a dipleg. Spent catalyst in the disengager is passed to a stripping section 311 where it is contacted with stripping steam from pipeline 312. The product vapor stripped from the spent catalyst is passed to the plenum chamber 310 after passing through the cyclone separator. The stripped spent catalyst is passed to a regenerator 314 through a standpipe 313, and main air is introduced into the regenerator through pipeline 316 to burn out the coke on the spent catalyst so as to regenerate the inactivated spent catalyst. The flue gas is passed to a flue gas turbine via pipeline 315. The regenerated catalyst is recycled to the bottom of reactor 302 via pipeline 317.

The reaction product (reaction product vapor) is passed to a subsequent fractionator 320 through a reactor vapor line 319 for separation, the separated hydrogen, methane and ethane are withdrawn through pipeline 321, ethylene is withdrawn through pipeline 322, propylene is withdrawn through pipeline 323, butylene is recycled to the bottom of the reactor 302 through pipeline 324 for further reaction, propane and butane are withdrawn through pipeline 325, and the unconverted oxygen-containing organic compound is withdrawn through pipeline 326 and optionally recycled to the lower middle part of the second reaction zone II of the reactor 302 for further reaction; the first catalytic cracking distillate oil is passed into an olefin separator 329 through pipeline 327 for separation, so as to obtain an olefin-depleted stream and an olefin-rich streams, the olefin-depleted stream is withdrawn through pipeline 331, and the olefin-rich stream is sent to the bottom of the second reaction zone II of the reactor 302 through pipeline 330 for further reaction; the second catalytic cracking distillate oil is passed into a hydrotreater 332 through pipeline 328, and a light component and a hydrogenated catalytic cracking distillate oil are obtained after separation, the light component is withdrawn through a pipe 318, and the hydrogenated catalytic cracking distillate oil is withdrawn through pipeline 333, and optionally mixed with the heavy feedstock oil and then sent to the bottom of the first reaction zone I of the reactor 302 for further reaction.

In particularly preferred embodiments, the present application provides the following technical solutions:

A1, a catalytic conversion method for maximizing the production of propylene, comprising the steps of:
- S1, contacting a heavy feedstock oil with a catalytic conversion catalyst having a temperature of 650° C. or higher, and carrying out a first catalytic conversion reaction in a first reaction zone of a catalytic conversion reactor to obtain a first mixed stream;
- S2, contacting a hydrocarbon oil feedstock having an olefin content of 50 wt % or higher with the first mixture flow in a second reaction zone of the catalytic conversion reactor, and carrying out a second catalytic conversion reaction to obtain reaction product vapor and a spent catalyst; the second reaction zone is located downstream of the first reaction zone;
- S3, carrying out a first separation on the reaction product vapor to obtain ethylene, propylene, butylene, a first catalytic cracking distillate oil and a second catalytic cracking distillate oil; the initial point of the first catalytic cracking distillate oil is more than 20° C., the final point of the second catalytic cracking distillate oil is less than 550° C., the cut point between the first catalytic cracking distillate oil and the second catalytic cracking distillate oil is between 140° C. and 250° C., and carrying out a second separation on the first catalytic cracking distillate oil to obtain an olefin-rich stream; and separately introducing the butylene and the olefin-rich stream into the catalytic conversion reactor for further reaction.

A2, the method according to Item A1, wherein in step S3, the butylene introduced into the catalytic conversion reactor for further reaction is contacted with the catalytic conversion catalyst prior to the heavy feedstock oil.

A3, the method according to Item A1, wherein the olefin in the olefin-rich stream is a C4+ olefin;
the olefin content of the olefin-rich stream is from 50 wt % to 100 wt %.

A4, the method according to Item A1, wherein the butylene is introduced into the first reaction zone of the catalytic conversion reactor for reaction and the olefin-rich stream is introduced into the second reaction zone of the catalytic conversion reactor for reaction.

A5, the method according to Item A1, wherein the catalytic conversion reactor further comprises a reaction zone A and a reaction zone B; the reaction zone A and the reaction zone B are sequentially arranged at the downstream of the second reaction zone;
the second separation comprises: separating from the first catalytic cracking distillate oil a first olefin-rich stream and a second olefin-rich stream; the cut point between the first stream and the second stream is between 140-200° C.;
the butylene is introduced into the first reaction zone for reaction;
the first stream is introduced into the reaction zone A for further reaction;
the second stream is introduced into the reaction zone B for further reaction.

A6, the method according to Item A1, wherein the method further comprises: regenerating the spent catalyst by coke burning to obtain a regenerated catalyst; and preheating the regenerated catalyst and then recycling to the catalytic conversion reactor.

A7, the method according to Item A1, wherein the method further comprises:
carrying out a hydrotreatment on the second catalytic cracking distillate oil to obtain a hydrogenated product, and separating a hydrogenated catalytic cracking distillate oil from the hydrogenated product;
introducing the hydrogenated catalytic cracking distillate oil into the first reaction zone for further reaction.

A8, the method according to Item A7, wherein,
The hydrotreatment conditions include: a hydrogen partial pressure of 3.0-20.0 MPa, a reaction temperature of 300-450° C., a hydrogen-to-oil volume ratio of 300-2000, and a volume space velocity of 0.1-3.0 $h^{-1}$.

A9, the method according to Item A1, wherein the catalytic conversion reactor is one selected from a riser reactor, a constant-linear-velocity fluidized bed, an equal-diameter fluidized bed, an ascending transfer line, and a descending transfer line, or a combination of two of them connected in series; the riser reactor is preferably a diameter-transformed riser reactor.

A10, the method according to Item A1, wherein the conditions of the first catalytic conversion reaction include: a reaction temperature of 500-800° C., a reaction pressure of 0.05-1 MPa, a reaction time of 0.01-100 seconds, and a weight ratio of the catalytic conversion catalyst to the heavy feedstock oil of (1-200):1;
the conditions of the second catalytic conversion reaction include: a reaction temperature of 400-680° C., a reaction pressure of 0.05-1 MPa, a reaction time of 0.01-100 seconds, and a weight ratio of the catalytic conversion catalyst to the hydrocarbon oil feedstock of (1-100):1;

preferably, the conditions of the first catalytic conversion reaction include: a reaction temperature of 510-780° C., a reaction pressure of 0.1-0.8 MPa, a reaction time of 0.1-80 seconds, and a weight ratio of the catalytic conversion catalyst to the heavy feedstock oil of (3-180):1;

the conditions of the second catalytic conversion reaction include: a reaction temperature of 450-650° C., a reaction pressure of 0.1-0.8 MPa, a reaction time of 0.1-80 seconds, and a weight ratio of the catalytic conversion catalyst to the hydrocarbon oil feedstock of (3-70):1.

A11, the method according to Item A1, wherein, the conditions for the further reaction of the butylene introduced into the catalytic reactor include: a reaction temperature of 650-800° C., a reaction pressure of 0.05-1 MPa, a reaction time of 0.01-10 seconds, and a weight ratio of the catalytic conversion catalyst to the butylene of (20-200):1;

preferably, the conditions include a reaction temperature of 680-780° C., a reaction pressure of 0.1-0.8 MPa, a reaction time of 0.05-8 seconds, and a weight ratio of the catalytic conversion catalyst to the butylene of (30-180):1.

A12, the method according to Item A1, wherein the hydrocarbon oil feedstock has an olefin content of 80 wt % or more; preferably 90 wt % or more; more preferably, the hydrocarbon oil feedstock is a pure olefin feedstock;

the heavy feedstock oil is a petroleum hydrocarbon and/or a mineral oil; the petroleum hydrocarbon is at least one selected from vacuum gas oil, atmospheric gas oil, coking gas oil, deasphalted oil, vacuum residuum, atmospheric residuum and heavy aromatic raffinate; the mineral oil is at least one selected from the group consisting of coal liquefaction oil, oil sand oil and shale oil.

A13, the method according to Item A1 or A12, wherein the olefins in the hydrocarbon oil feedstock are derived from C4+ fractions produced by dehydrogenation of an alkane feedstock, C4+ fractions from a catalytic cracking unit in an oil refinery, C4+ fractions from a steam cracking unit in an ethylene plant, a C4+ olefin-rich byproduct fraction of an MTO process, and a C4+ olefin-rich byproduct fraction of an MTP process;

the alkane feedstock is at least one selected from the group consisting of naphtha, aromatic raffinate and light hydrocarbons.

A 14, the method according to Item A1, wherein the catalytic conversion catalyst comprises 1-50 wt % of a molecular sieve, 5-99 wt % of an inorganic oxide, and 0-70 wt % of a clay, based on the weight of the catalytic conversion catalyst;

the molecular sieve comprises one or more of a macroporous molecular sieve, a mesoporous molecular sieve and a microporous molecular sieve;

the catalytic conversion catalyst further comprises 0.1 to 3 wt % of an active metal, based on the weight of the catalytic conversion catalyst; the active metal is one or more selected from the group consisting of Group VIII metal, Group IVA metal and rare earth metal.

B1, a catalytic conversion method for maximizing the production of propylene, comprising the steps of:

S1, contacting a heavy feedstock oil with a catalytic conversion catalyst having a temperature of 650° C. or higher, and carrying out a first catalytic conversion reaction under first catalytic conversion conditions in a first reaction zone of a catalytic conversion reactor to obtain a first mixed stream;

S2, contacting a hydrocarbon oil feedstock having an olefin content of 50 wt % or higher and an oxygen-containing organic compound feedstock with the first mixed stream from the first reaction zone in a second reaction zone of the catalytic conversion reactor, and carrying out a second catalytic conversion reaction under second catalytic conversion conditions to obtain reaction product vapor and a spent catalyst;

S3, carrying out a first separation on the reaction product vapor to obtain ethylene, propylene, butylene, an oxygen-containing organic compound, a first catalytic cracking distillate oil and a second catalytic cracking distillate oil; the initial boiling point of the first catalytic cracking distillate oil is from more than 20° C. to less than 140° C., the final boiling point of the second catalytic cracking distillate oil is from more than 250° C. to less than 550° C., and the cut point between the first catalytic cracking distillate oil and the second catalytic cracking distillate oil is between 140° C. and 250° C.;

carrying out a second separation on the first catalytic cracking distillate oil to obtain an olefin-rich stream;

S4, recycling the olefin-rich stream to the catalytic conversion reactor for further reaction.

B2, the method according to Item B1, wherein the method comprises:

passing the reaction product vapor to a product fractionator for first separation, and separating out ethylene, propylene, butylene, the oxygen-containing organic compound, the first catalytic cracking distillate oil and the second catalytic cracking distillate oil;

passing the first catalytic cracking distillate oil into an olefin separator for second separation, and separating out the olefin-rich stream;

recycling the olefin-rich stream to the first reaction zone of the catalytic conversion reactor for further reaction.

B3, the method according to Item B1 or B2, wherein the method further comprises: recycling the separated butylene to the first reaction zone of the catalytic conversion reactor for further reaction;

preferably, the butylene recycled to the catalytic conversion reactor for further reaction is contacted with the catalytic conversion catalyst before the heavy feedstock oil.

B4, the method according to Item B3, wherein the conditions for the further reaction of the butylene recycled to the catalytic reactor include: a reaction temperature of 650-800° C., a reaction pressure of 0.05-1 MPa, a reaction time of 0.01-10 seconds, and a weight ratio of the catalytic conversion catalyst to the recycled butylene of (20-200):1;

preferably, the conditions include a reaction temperature of 680-780° C., a reaction pressure of 0.1-0.8 MPa, a reaction time of 0.05-8 seconds, and a weight ratio of the catalytic conversion catalyst to the recycled butylene of (30-180):1.

B5, the method according to Item B1, wherein the first catalytic conversion conditions include: a reaction temperature of 500-800° C., a reaction pressure of 0.05-1 MPa, a reaction time of 0.01-100 seconds, and a weight ratio of the catalytic conversion catalyst to the heavy feedstock oil of (1-200):1;

preferably, the first catalytic conversion conditions include: a reaction temperature of 510-780° C., a reaction pressure of 0.1-0.8 MPa, a reaction time of 0.1-80 seconds, and a weight ratio of the catalytic conversion catalyst to the heavy feedstock oil of (3-180):1.

B6, the method according to Item B1 or B5, wherein the second catalytic conversion conditions include: a reaction temperature of 300-680° C., a reaction pressure of 0.01-1 MPa, a reaction time of 0.01-100 seconds, and a weight ratio of the catalytic conversion catalyst to the hydrocarbon oil feedstock of (1-100):1; a weight ratio of the catalytic conversion catalyst to the oxygen-containing organic compound of (1-100):1;
  preferably, the second catalytic conversion conditions include: a reaction temperature of 400-650° C., a reaction pressure of 0.05-1 MPa, a reaction time of 0.1-80 seconds, and a weight ratio of the catalytic conversion catalyst to the hydrocarbon oil feedstock of (3-70):1; a weight ratio of the catalytic conversion catalyst to the oxygen-containing organic compound feedstock of (3-50):1;
  preferably, the reaction temperature of the first catalytic conversion reaction is 0 to 380° C. higher than the reaction temperature of the second catalytic conversion reaction, and further preferably, the reaction temperature of the first catalytic conversion reaction is 10 to 370° C. higher than the reaction temperature of the second catalytic conversion reaction.

B7, the method according to Item B1 or B5, wherein the second reaction zone is divided along the flow direction of the reaction stream into an upstream part of the second reaction zone and a downstream part of the second reaction zone, bounded by the feeding position of the oxygen-containing organic compound feedstock, the downstream part of the second reaction zone is downstream of the feeding position of the oxygen-containing organic compound feedstock; the method further comprises the following steps:
  contacting the first mixed stream from the first reaction zone with the hydrocarbon oil feedstock having an olefin content of 50 wt % or higher in the upstream part of the second reaction zone and carrying out a catalytic conversion reaction to obtain a second mixed stream; and then contacting the second mixed stream with the oxygen-containing organic compound feedstock in the downstream part of the second reaction zone and carrying out a catalytic conversion reaction to obtain reaction product vapor and a spent catalyst.

B8, the method according to Item B7, wherein the catalytic conversion conditions for the reaction between the hydrocarbon oil feedstock and the first mixed stream in the upstream part of the second reaction zone include:
  a reaction temperature of 400-680° C., preferably 450-650° C.;
  a reaction pressure of 0.05-1 MPa, preferably 0.1-0.8 MPa;
  a reaction time of 0.01-100 seconds, preferably 0.1-80 seconds;
  a weight ratio of the catalytic conversion catalyst to the hydrocarbon oil feedstock of (1-100):1, preferably (3-70):1;
  the catalytic conversion conditions for the reaction between the oxygen-containing organic compound feedstock and the second mixed stream in the downstream part of the second reaction zone include:
  a reaction temperature of 300-550° C., preferably 400-530° C.;
  a reaction pressure of 0.01-1 MPa, preferably 0.05-1 MPa;
  a reaction time of 0.01-100 seconds, preferably 0.1-80 seconds;
  a weight ratio of the catalytic conversion catalyst to the oxygen-containing organic compound feedstock of (1-100):1, preferably (3-50):1;
  the reaction temperature in the upstream part of the second reaction zone is 0 to 250° C. higher than the reaction temperature in the downstream part of the second reaction zone, preferably the reaction temperature in the upstream part of the second reaction zone is 10 to 240° C. higher than the reaction temperature in the downstream part of the second reaction zone.

B9, the method according to Item B1, wherein the method further comprises: recycling the separated oxygen-containing organic compound to the second reaction zone of the catalytic conversion reactor for further reaction.

B10, the method according to any one of Items B1-B9, wherein the catalytic conversion reactor is a riser reactor, preferably a diameter-transformed riser reactor.

B11, the method according to Item B1, wherein the method further comprises: regenerating the spent catalyst by coke burning to obtain a regenerated catalyst; recycling the regenerated catalyst to the first reaction zone of the catalytic conversion reactor as the catalytic conversion catalyst.

B12, the method according to Item B1, wherein the heavy feedstock oil is a petroleum hydrocarbon and/or a mineral oil; the petroleum hydrocarbon is at least one selected from vacuum gas oil, atmospheric gas oil, coking gas oil, deasphalted oil, vacuum residuum, atmospheric residuum and heavy aromatic raffinate; the mineral oil is at least one selected from the group consisting of coal liquefaction oil, oil sand oil and shale oil;
  the hydrocarbon oil feedstock has an olefin content of 80 wt % or more; preferably 90 wt % or more; more preferably, the hydrocarbon oil feedstock is a pure olefin feedstock;
  optionally, the oxygen-containing organic compound feedstock comprises at least one of methanol, ethanol, dimethyl ether, methyl ethyl ether, and diethyl ether.

B13, the method according to Item B1 or B12, wherein the olefins in the hydrocarbon oil feedstock are derived from at least one of a C5+ fraction produced by an alkane dehydrogenation unit, a C5+ fraction produced by a catalytic cracking unit in an oil refinery, a C5+ fraction produced by a steam cracking unit in an ethylene plant, a C5+ olefin-rich byproduct fraction of an MTO process, and a C5+ olefin-rich byproduct fraction of an MTP process;
  optionally, the alkane feedstock of the alkane dehydrogenation unit is derived from at least one of naphtha, aromatic raffinate and other light hydrocarbons.

B14. the method according to Item B1, wherein the catalytic conversion catalyst comprises 1-50 wt % of a molecular sieve, 5-99 wt % of an inorganic oxide, and 0-70 wt % of a clay, based on the weight of the catalytic conversion catalyst;
  the molecular sieve comprises one or more of a macroporous molecular sieve, a mesoporous molecular sieve and a microporous molecular sieve;
  the catalytic conversion catalyst further comprises 0.1 to 3 wt % of an active metal, based on the weight of the catalytic conversion catalyst; the active metal is one or more selected from the group consisting of Group VIII metal, Group IVA metal and rare earth metal.

B15, the method according to Item B1, wherein the method further comprises: carrying out a hydrotreatment on the second catalytic cracking distillate oil under hydrogenation conditions, to obtain a hydrogenated catalytic cracking distillate oil;
   introducing the hydrogenated catalytic cracking distillate oil into a first reaction zone of the catalytic conversion reactor for further reaction;
   wherein the hydrotreatment conditions include: a hydrogen partial pressure of 3.0 to 20.0 MPa, a reaction temperature of 300-450° C., a hydrogen-to-oil volume ratio of 300-2000, and a volume space velocity of 0.1 to 3.0 $h^{-1}$;
   optionally, the hydrogenation catalyst comprises 20-90 wt % of a carrier, 10-80 wt % of a supported metal, and 0-10 wt % of an additive, based on the total weight of the hydrogenation catalyst;
   the carrier is alumina and/or amorphous silica-alumina, the additive is at least one selected from the group consisting of fluorine, phosphorus, titanium and platinum, and the supported metal is Group VIB metal and/or Group VIII metal;
   preferably, the Group VIB metal is Mo or/and W, and the Group VIII metal is Co or/and Ni.
B16, the method according to Item B1, wherein the olefin in the olefin-rich stream is a C5+ olefin;
   the olefin-rich stream has a C5+ olefin content of 50 wt % or more, preferably 80 wt % or more.

EXAMPLES

The present application will be described in further detail below with reference to examples. The feedstocks used in the examples are all commercially available.
Feedstock and Catalyst
The properties of Heavy feedstock oil a and Heavy feedstock oil b used in the following examples are shown in Tables 1-1 and 1-2, respectively.

TABLE 1-1

Properties of Heavy feedstock oil a

| Properties | Heavy feed oil a |
|---|---|
| Density (20° C.)/(kg/m³) | 859.7 |
| Conradson carbon residue, wt % | 0.07 |
| C, wt % | 85.63 |
| H, wt % | 13.45 |
| S, wt % | 0.077 |
| N, wt % | 0.058 |
| Fe, μg/g | 2.3 |
| Na, μg/g | 0.6 |
| Ni, μg/g | 4.9 |
| V, μg/g | 0.4 |
| Hydrocarbon composition, wt % | |
| Saturates | 58.1 |
| Aromatics | 26.3 |
| Resins | 15.3 |
| Asphaltenes | 0.3 |

TABLE 1-2

Properties of Heavy feedstock oil b

| Properties | Heavy feed oil b |
|---|---|
| Density (20° C.)/(kg/m³) | 901.5 |
| Conradson carbon residue, wt % | 4.9 |
| H, wt % | 12.86 |
| S, wt % | 0.16 |

TABLE 1-2-continued

Properties of Heavy feedstock oil b

| Properties | Heavy feed oil b |
|---|---|
| N, wt % | 0.26 |
| Ni, μg/g | 6.2 |
| Hydrocarbon composition, wt % | |
| Saturates | 54.8 |
| Aromatics | 28.4 |
| Resins | 16.0 |
| Asphaltenes | 0.8 |

The preparation or source of the various catalysts used in the following examples and comparative examples is as follows:
Catalytic Conversion Catalyst A
   It was prepared as follows: 969 g of halloysite (product of China Kaolin Clay Co., Ltd., with solid content of 73%) was slurried with 4300 g of decationized water, 781 g of pseudo-boehmite (product of CHALCO Shandong Co., Ltd, with solid content of 64%) and 144 ml of hydrochloric acid (with concentration of 30% and specific gravity of 1.56) were added thereto and stirred evenly, the mixture was kept stand and aged for 1 hour at 60° C., while maintaining the pH value at 2-4, the mixture was cooled to room temperature, and 5000 g of prepared slurry was added, which comprised 1600 g of mesoporous ZSM-5 zeolite and macroporous Y molecular sieve (produced by Qilu Branch of Sinopec Catalyst Co., Ltd.), and the weight ratio of the mesoporous ZSM-5 zeolite to the macroporous Y molecular sieve was 9:1. The mixture was stirred uniformly, spray dried, and washed to remove free Na+ to obtain a catalyst. The catalyst obtained was aged at 800° C. with 100% steam, the aged catalyst was designated as Catalyst A. The properties of Catalyst A are shown in Table 2.
   Catalytic conversion catalyst B: an industrial product available from Qilu Branch of Sinopec Catalyst Co., Ltd. under a trade name of CEP-1, the properties of which are shown in Table 2.
   Catalytic conversion catalyst C: an industrial product available from Qilu Branch of Sinopec Catalyst Co., Ltd. under a trade name of CHP-1, the properties of which are shown in Table 2.
Hydrotreating Catalyst D
   It was prepared as follows: ammonium metatungstate $((NH_4)_2W_4O_{13} \cdot 18H_2O$, chemically pure) and nickel nitrate $(Ni(NO_3)_2 \cdot 18H_2O$, chemically pure) were weighed and mixed with water to obtain a 200 ml solution. The solution was added to 50 g of alumina carrier, impregnated for 3 hours at room temperature, the impregnation solution was treated with ultrasonic waves for 30 minutes during the impregnation, cooled, filtered, and dried in a microwave oven for about 15 minutes. The catalyst comprises the following components: 30.0 wt % of $WO_3$, 3.1 wt % of NiO, and the balance of alumina, and is designated as Catalyst D.
Hydrodesulfurization Catalyst E
   It was prepared as follows: 1000 g of pseudo-boehmite produced by ChangLing Branch of Sinopec Catalyst Co., Ltd. was weighed, 1000 ml of aqueous solution comprising 10 ml of nitric acid (chemically pure) was added thereto, shaped by extrusion molding on a double-screw extruder, dried at 120° C. for 4 hours, and calcined at 800° C. for 4 hours to obtain a catalyst carrier. The resultant was impregnated with 900 ml of aqueous solution comprising 120 g of ammonium fluoride for 2 hours, dried for 3 hours at 120° C., and calcined for 3 hours at 600° C.; after cooling to room temperature, the resultant was impregnated with 950 ml of an aqueous solution comprising 133 g of ammonium metamolybdate for 3 hours, dried at 120° C. for 3 hours, and calcined at 600° C. for 3 hours; and after cooling to room temperature, the resulting was impregnated with 900 ml of an aqueous solution comprising 180 g of nickel nitrate and 320 g of ammonium metatungstate for 4 hours, and the fluorinated alumina carrier was impregnated with a mixed aqueous solution comprising 0.1 wt % of ammonium metamolybdate (chemically pure) and 0.1 wt % of nickel nitrate (chemically pure) relative to the catalyst carrier for 4 hours, dried at 120° C. for 3 hours, and calcined at 600° C. for 4 hours, to obtain Catalyst E.

TABLE 2

Properties of Catalysts A, B and C

| Catalyst | A | B | C |
|---|---|---|---|
| Chemical composition/wt % | | | |
| $Al_2O_3$ | 49.2 | 26.5 | 46.3 |
| $Na_2O$ | 0.07 | 0.19 | 0.04 |
| Physical Properties | | | |
| Specific surface area/($m^2 \cdot g^{-1}$) | / | 132 | 153 |
| Bulk density/($g \cdot cm^{-3}$) | 0.79 | 0.45 | 0.86 |
| Abrasion index/(% · $h^{-1}$) | 1.1 | 4.2 | 1.0 |
| Size distribution/wt % | | | |
| 0-40 μm | 14.2 | 7.3 | 17.9 |
| 40-80 μm | 53.8 | 43.7 | 41.4 |
| >80 μm | 320 | 49.0 | 40.7 |

Example 1

An experiment was carried out on a pilot plant of a riser reactor according to the scheme shown in FIG. 1 as follows:

Heavy feedstock oil a was contacted with catalytic conversion Catalyst A at the bottom of a first reaction zone for reaction under conditions including a reaction temperature of 600° C., a reaction pressure of 0.1 MPa, a reaction time of 3 s, and a weight ratio of the catalyst to the feedstock of 5:1. 1-pentene feedstock was contacted with the catalytic conversion Catalyst A from the first reaction zone at the bottom of the second reaction zone for reaction under conditions including a reaction temperature of 530° C., a reaction pressure of 0.1 MPa, a reaction time of 10 s, and a weight ratio of the catalyst to the 1-pentene feedstock of 45:1.

The resulting reaction product was separated from the spent catalyst, the spent catalyst was regenerated by coke burning in a regenerator, and the reaction product was separated to obtain ethylene, propylene, butylene, an olefin-rich stream, a second catalytic cracking distillate oil with a boiling point of more than 250° C., and the like.

The second catalytic cracking distillate oil was reacted with hydrogenation Catalyst D under conditions including a temperature of 350° C., a hydrogen partial pressure of 18 MPa, a volume space velocity of 1.5 $h^{-1}$, and a hydrogen-to-oil volume ratio of 1500 to obtain a hydrogenated catalytic cracking distillate oil.

The separated butylene was recycled to the bottom of the riser reactor for further cracking, under conditions including a reaction temperature of 650° C., a weight ratio of the catalyst to the butylene of 100:1, and a reaction time of 0.2 s; the olefin-rich stream was recycled to the bottom of the second reaction zone for further cracking; the hydrogenated catalytic cracking distillate oil was mixed with the heavy feedstock oil and then recycled to the first reaction zone for reaction. The reaction conditions and product distribution are listed in Table 3.

Comparative Example 1

An experiment was carried out on a pilot plant of a riser reactor as described Example 1, expect that no 1-pentene was added at the bottom of the second reaction zone and no olefin-rich stream was recycled to the riser reactors, as follows:

Heavy feedstock oil a was contacted with catalytic conversion Catalyst A at the bottom of a first reaction zone for reaction under conditions including a reaction temperature of 600° C., a reaction pressure of 0.1 MPa, a reaction time of 3 s, and a weight ratio of the catalyst to the feedstock of 5:1.

The resulting reaction product was separated from the spent catalyst, the spent catalyst was regenerated by coke burning in a regenerator, and the regenerated catalyst was recycled to the bottom of the riser reactor; the reaction product was separated to obtain ethylene, propylene, butylene and a catalytic cracking distillate oil with a boiling point of more than 250° C.

The catalytic cracking distillate oil was reacted with hydrogenation Catalyst D under conditions including a temperature of 350° C., a hydrogen partial pressure of 18 MPa, a volume space velocity of 1.5 $h^{-1}$ and a hydrogen-to-oil volume ratio of 1500 to obtain a hydrogenated catalytic cracking distillate oil.

The separated butylene was recycled to the bottom of the riser reactor for further cracking, under conditions including a reaction temperature of 650° C., a weight ratio of the catalyst to the butylene of 100:1, a reaction time of 0.2 s; the hydrogenated catalytic cracking distillate oil was mixed with the heavy feedstock oil and then recycled to the first reaction zone for reaction. The reaction conditions and product distribution are listed in Table 3.

Example 2

An experiment was carried out on a pilot plant of a riser reactor according to the scheme shown in FIG. 1 as follows:

Heavy feedstock oil a was contacted with catalytic conversion Catalyst A at the bottom of a first reaction zone for reaction under conditions including a reaction temperature of 600° C., a reaction pressure of 0.1 MPa, a reaction time of 3 s, and a weight ratio of the catalyst to the feedstock of 5:1.

The resulting reaction product was separated from the spent catalyst, the spent catalyst was regenerated by coke burning in a regenerator, and the regenerated catalyst was recycled to the bottom of the riser reactor; the reaction product was separated to obtain ethylene, propylene, butylene, an olefin-rich stream, a second catalytic cracking distillate oil with a boiling point of more than 250° C., and the like.

The second catalytic cracking distillate oil was reacted with hydrogenation Catalyst D under conditions including a temperature of 350° C., a hydrogen partial pressure of 18 MPa, a volume space velocity of 1.5 $h^{-1}$ and a hydrogen-to-oil volume ratio of 1500 to obtain a hydrogenated catalytic cracking distillate oil.

The separated butylene was recycled to the bottom of the riser reactor for further cracking, under conditions including a reaction temperature of 650° C., a weight ratio of the catalyst to the feedstock of 100:1, and a reaction time of 0.2 s; the olefin-rich stream was recycled to the bottom of the second reaction zone for further cracking under conditions including a reaction temperature of 530° C., a reaction pressure of 0.1 MPa, and a reaction time of 10 s; the hydrogenated catalytic cracking distillate oil was mixed with the heavy feedstock oil and then recycled to the first reaction zone for reaction. The reaction conditions and product distribution are listed in Table 3.

Comparative Example 2

An experiment was carried out on a pilot plant of a riser reactor, in which Heavy feedstock oil a was contacted with catalytic conversion Catalyst B at the bottom of the riser reactor for reaction under conditions including a reaction temperature of 610° C., a reaction pressure of 0.1 MPa, a reaction time of 6 s, and a weight ratio of the catalyst to the feedstock of 16.9:1.

The resulting reaction product was separated from the spent catalyst, the spent catalyst was regenerated by coke burning in a regenerator, and the regenerated catalyst was recycled to the bottom of the riser reactor; the reaction product was not subjected to hydrotreatment or further reaction after being separated. The reaction conditions and product distribution are listed in Table 3.

Example 3

An experiment was carried out as described in Example 2, except that heavier Heavy feedstock oil b was used, the second catalytic cracking distillate oil with a boiling point of greater than 250° C. was contacted with hydrodesulfurization Catalyst E in the hydrodesulfurization reactor, and reacted under conditions including a reaction pressure of 6.0 MPa, a reaction temperature of 350° C., a hydrogen-to-oil volume ratio of 350, and a volume space velocity of 2.0 hours, to obtain a low-sulfur hydrogenated catalytic cracking distillate oil which was withdrawn as a light oil component without recycling to the riser reactor for further reaction. The reaction conditions and product distribution are listed in Table 3.

Comparative Example 3

An experiment was carried out on a pilot plant of a riser reactor, in which Heavy feedstock oil b was reacted with catalytic conversion Catalyst C at the bottom of the riser reactor for reaction under conditions including a reaction temperature of 530° C., a reaction pressure of 0.1 MPa, a reaction time of 6 s, and a weight ratio of the catalyst to the feedstock of 5:1.

The resulting reaction product was separated from the spent catalyst, the spent catalyst was regenerated by coke burning in a regenerator, and the regenerated catalyst was recycled to the bottom of the riser reactor; the reaction product obtained after separation was not recycled to the riser reactor for further reaction, and the hydrotreatment of the second catalytic cracking distillate oil was the same as that in Example 3. The reaction conditions and product distribution are listed in Table 3.

Example 4

An experiment was carried out as described in Example 1, except that the reaction conditions shown in Table 3 were employed. The reaction conditions and product distribution are listed in Table 3.

Example 5

An experiment was carried out as described in Example 1, except that the reaction conditions shown in Table 3 were employed. The reaction conditions and product distribution are listed in Table 3.

Example 6

An experiment was carried out as described in Example 1, except that the reaction conditions shown in Table 3 were employed. The reaction conditions and product distribution are listed in Table 3.

TABLE 3

Reaction conditions and product distribution for Examples 1-6 and Comparative Examples 1-3

| | Ex. 1 | Comp. Ex. 1 | Ex. 2 | Comp. Ex. 2 | Ex. 3 | Comp. Ex. 3 | Ex. 4 | Ex. 5 | Ex. 6 |
|---|---|---|---|---|---|---|---|---|---|
| First reaction zone | | | | | | | | | |
| Catalytic conversion catalyst | Catalyst A | Catalyst A | Catalyst A | Catalyst B | Catalyst A | Catalyst C | Catalyst A | Catalyst A | Catalyst A |
| Feedstock | Feedstock oil a | Feedstock oil a | Feedstock oil a | Feedstock oil a | Feedstock oil b | Feedstock oil b | Feedstock oil a | Feedstock oil a | Feedstock oil a |
| Catalyst temperature, ° C. | 700 | 700 | 700 | 680 | 700 | 650 | 680 | 750 | 660 |
| Reaction temperature, ° C. | 600 | 600 | 600 | 610 | 600 | 530 | 580 | 700 | 510 |
| Catalyst-to-oil ratio | 5 | 5 | 5 | 16.9 | 5 | 5 | 5 | 5 | 5 |
| Reaction time, s | 3 | 3 | 3 | 6 | 3 | 6 | 3 | 3 | 3 |
| Second reaction zone | | | | | | | | | |
| Feedstock | 1-pentene | — | Recycled olefin-rich stream | — | Recycled olefin-rich stream | — | 1-pentene | 1-pentene | 1-pentene |
| Reaction temperature, ° C. | 530 | | 530 | | 530 | | 500 | 580 | 450 |
| Catalyst-to-oil ratio | 45 | | — | | — | | 45 | 45 | 45 |
| Reaction time, s | 10 | | 10 | | 10 | | 10 | 10 | 10 |
| Butylene refining | | | | | | | | | |
| Reaction temperature, ° C. | 650 | 650 | 650 | | 650 | | 650 | 730 | 650 |
| Catalyst-to-oil ratio | 100 | 100 | 100 | | 100 | | 100 | 100 | 100 |
| Reaction time, s | 0.2 | 0.2 | 0.2 | | 0.2 | | 0.2 | 0.2 | 0.2 |
| Hydrogenation unit | | | | | | | | | |
| Catalyst | Catalyst D | Catalyst D | Catalyst D | — | Catalyst E | Catalyst E | Catalyst D | Catalyst D | Catalyst D |

TABLE 3-continued

Reaction conditions and product distribution for Examples 1-6 and Comparative Examples 1-3

|  | Ex. 1 | Comp. Ex. 1 | Ex. 2 | Comp. Ex. 2 | Ex. 3 | Comp. Ex. 3 | Ex. 4 | Ex. 5 | Ex. 6 |
|---|---|---|---|---|---|---|---|---|---|
| Temperature, °C. | 350 | 350 | 350 |  | 350 | 350 | 350 | 350 | 350 |
| Hydrogen-to-oil volume ratio | 1500 | 1500 | 1500 |  | 350 | 350 | 1500 | 1500 | 1500 |
| Yield, W % |  |  |  |  |  |  |  |  |  |
| Hydrogen + methane + ethane | 5.32 | 4.95 | 5.07 | 12.58 | 5.38 | 1.56 | 4.63 | 5.97 | 4.99 |
| Ethylene | 18.64 | 10.27 | 17.52 | 13.71 | 17.83 | 1.44 | 10.18 | 21.94 | 11.90 |
| Propylene | 50.66 | 25.65 | 43.69 | 21.45 | 44.02 | 10.11 | 37.20 | 51.17 | 29.76 |
| Butylene | — | — | — | 12.24 | — | 8.78 | — | — | — |
| Propane + butane | 4.19 | 3.56 | 4.02 | 3.76 | 4.31 | 5.91 | 3.48 | 4.01 | 3.51 |
| Benzene | 3.66 | 1.24 | 3.15 | 3.61 | 4.27 | 4.84 | 3.11 | 3.17 | 1.04 |
| Toluene | 1.59 | 0.82 | 1.48 | 3.15 | 1.66 | 3.17 | 1.02 | 2.34 | 0.99 |
| Xylene | 0.47 | 0.24 | 0.54 | 2.92 | 1.02 | 1.03 | 0.44 | 1.92 | 0.52 |
| Light oil | 10.43 | 48.26 | 19.30 | 16.91 | 15.83 | 58.17 | 35.19 | 3.10 | 42.96 |
| Coke | 5.04 | 5.01 | 5.23 | 9.67 | 5.68 | 4.99 | 4.75 | 6.38 | 4.33 |
| Total | 100.00 | 100.00 | 100.00 | 100.00 | 100.00 | 100.00 | 100.00 | 100.00 | 100.00 |
| Ethylene/propylene | 0.37 | 0.40 | 0.40 | 0.64 | 0.41 | 0.14 | 0.27 | 0.43 | 0.40 |
| Ethylene + propylene | 69.30 | 35.92 | 61.21 | 35.16 | 61.85 | 11.55 | 47.38 | 73.11 | 41.66 |

It can be seen from the results shown in Table 3 that the cracking of olefin feedstock at high temperature results in a higher propylene yield, and the ethylene yield is increased at the same time, and the higher the olefin content in the feedstock, the better the effect of improvement.

Example 7

An experiment was carried out on a pilot plant of a riser reactor according to the scheme shown in FIG. 2 as follows:

Heavy feedstock oil a was contacted with catalytic conversion Catalyst A at the bottom of a first reaction zone I for reaction under conditions including a reaction temperature of 600° C., a reaction pressure of 0.1 MPa, a reaction time of 3 s, and a weight ratio of the catalyst to the feedstock of 5:1. 1-octene feedstock was contacted with the catalytic conversion Catalyst A from the first reaction zone at the bottom of the second reaction zone for reaction under conditions including a reaction temperature of 530° C., a reaction pressure of 0.1 MPa, a reaction time of 10 s, and a weight ratio of the catalyst to the 1-octene of 45:1.

The resulting reaction product was separated from the spent catalyst, the spent catalyst was regenerated by coke burning in a regenerator, and the regenerated catalyst was recycled to the bottom of the riser reactor; the reaction product was separated to obtain ethylene, propylene, butylene, a first olefin-rich stream, a second olefin-rich stream, a second catalytic cracking distillate oil having a boiling point of more than 250° C., and the like.

The second catalytic cracking distillate oil was reacted with hydrogenation Catalyst D under conditions including a temperature of 350° C., a hydrogen partial pressure of 18 MPa, a volume space velocity of 1.5 h$^{-1}$ and a hydrogen-to-oil volume ratio of 1500 to obtain a hydrogenated catalytic cracking distillate oil.

The separated butylene was recycled to the bottom of the riser reactor for further cracking, under conditions including a reaction temperature of 650° C., and a weight ratio of the catalyst to the feedstock of 100:1, a reaction time of 0.2 s; the first olefin-rich stream having a boiling point of less than 140° C. (namely a stream comprising small molecular olefins) was recycled to the bottom of the second reaction zone for further cracking; the second olefin-rich stream having a boiling point of more than 140° C. (namely a stream comprising large molecular olefins) to the bottom of the third reaction zone for further cracking, under conditions including a reaction temperature of 500° C., and a reaction time of 10 s; the hydrogenated catalytic cracking distillate oil was mixed with the heavy feedstock oil and then recycled to the first reaction zone for reaction. The reaction conditions and product distribution are listed in Table 4.

Example 8

An experiment was carried out on a pilot plant of a riser reactor, according to the scheme shown in FIG. 3, as follows:

Heavy feedstock oil a was contacted with catalytic conversion Catalyst A at the bottom of a first reaction zone for reaction under conditions including a reaction temperature of 600° C., a reaction pressure of 0.1 MPa, a reaction time of 3 s, and a weight ratio of the catalyst to the feedstock of 5:1; 1-pentene feedstock was contacted with the catalytic conversion Catalyst A from the first reaction zone at the bottom of the second reaction zone for reaction under conditions including a reaction temperature of 530° C., a reaction pressure of 0.1 MPa, a reaction time of 6 s, and a weight ratio of the catalyst to the 1-pentene of 45:1. Methanol was introduced into a lower middle part of the second reaction zone for reaction under conditions including a reaction temperature of 500° C., a reaction pressure of 0.1 MPa, a reaction time of 3 seconds, and a weight ratio of the catalyst to methanol of 10:1.

The resulting reaction product was separated from the spent catalyst, the spent catalyst was regenerated by coke burning in a regenerator, and the reaction product was separated to obtain ethylene, propylene, butylene, an olefin-rich stream, a second catalytic cracking distillate oil with a boiling point of more than 250° C., and the like.

The second catalytic cracking distillate oil was reacted with hydrogenation Catalyst D under conditions including a temperature of 350° C., a hydrogen partial pressure of 18 MPa, a volume space velocity of 1.5 h$^{-1}$ and a hydrogen-to-oil volume ratio of 1500 to obtain a hydrogenated catalytic cracking distillate oil.

The separated butylene was recycled to the bottom of the riser reactor for further cracking, under conditions including a reaction temperature of 650° C., a weight ratio of the catalyst to the butylene of 100:1, a reaction time of 0.2 s; the olefin-rich stream was recycled to the bottom of the second reaction zone for further cracking; the hydrogenated catalytic cracking distillate oil was mixed with the heavy feedstock oil and then recycled to the first reaction zone for reaction. The reaction conditions and product distribution are listed in Table 4.

TABLE 4

Reaction conditions and product distribution for Examples 7-8

|  | Example 7 | Example 8 |
|---|---|---|
| *First reaction zone* | | |
| Catalytic conversion catalyst | Catalyst A | Catalyst A |
| Feedstock | Feedstock oil a | Feedstock oil a |
| Catalyst temperature, ° C. | 700 | 700 |
| Reaction temperature, ° C. | 600 | 600 |
| Catalyst-to-oil ratio | 5 | 5 |
| Reaction time, s | 3 | 3 |
| *Second reaction zone* | | |
| Feedstock | 1-octene/small molecule olefin | 1-pentene/methanol |
| Reaction temperature, ° C. | 530 | 530/500 |
| Catalyst-to-oil ratio | 45 | 45/10 |
| Reaction time, s | 10 | 6/3 |
| *Third reaction zone* | | |
| Feedstock | Large molecular olefins | — |
| Reaction temperature, ° C. | 500 | |
| Catalyst-to-oil ratio | — | |
| Reaction time, s | 10 | |
| *Butylene refining* | | |
| Reaction temperature, ° C. | 650 | 650 |
| Catalyst-to-oil ratio | 100 | 100 |
| Reaction time, s | 0.2 | 0.2 |
| *Hydrogenation unit* | | |
| Catalyst | Catalyst D | Catalyst D |
| Temperature, ° C. | 350 | 350 |
| Hydrogen-to-oil volume ratio | 1500 | 1500 |
| *Yield, W %* | | |
| Hydrogen + methane + ethane | 5.10 | 4.73 |
| Ethylene | 19.72 | 20.55 |
| Propylene | 53.77 | 48.98 |
| Propane + butane | 3.55 | 3.48 |
| Benzene | 3.20 | 2.14 |
| Toluene | 1.41 | 1.52 |
| Xylene | 0.65 | 0.49 |
| Light oil | 7.54 | 13.00 |
| Coke | 5.06 | 5.11 |
| Total | 100.00 | 100.00 |
| Ethylene/propylene | 0.37 | 0.42 |
| Ethylene + propylene | 73.49 | 69.53 |

As can be seen from the data shown in Table 4, the methods of Examples 7 and 8 of the present application further improved the overall yield of propylene and ethylene, particularly the yield of ethylene, and reduced the overall yield of hydrogen, methane and ethane, as compared to Example 1.

The present application is illustrated in detail hereinabove with reference to preferred embodiments, but is not intended to be limited to those embodiments. Various modifications may be made following the inventive concept of the present application, and these modifications shall be within the scope of the present application.

It should be noted that the various technical features described in the above embodiments may be combined in any suitable manner without contradiction, and in order to avoid unnecessary repetition, various possible combinations are not described in the present application, but such combinations shall also be within the scope of the present application.

In addition, the various embodiments of the present application can be arbitrarily combined as long as the combination does not depart from the spirit of the present application, and such combined embodiments should be considered as the disclosure of the present application.

The invention claimed is:

1. A fluidized catalytic conversion method comprising the steps of:
   1) Introducing a heavy feedstock oil into a first reaction zone of a fluidized catalytic conversion reactor, contacting with a catalytic conversion catalyst having a temperature of 650° C. or higher, and reacting under first catalytic conversion reaction conditions;
   2) Introducing a hydrocarbon oil feedstock having an olefin content of 50 wt % or more into a second reaction zone of the fluidized catalytic conversion reactor downstream of the first reaction zone, contacting with the catalytic conversion catalyst from the first reaction zone after the reaction of step 1), and reacting under second catalytic conversion conditions;
   3) Separating the effluent of the fluidized catalytic conversion reactor to obtain reaction products and a spent catalyst, and carrying out a first separation on the reaction products to obtain ethylene, propylene, butylene, a first catalytic cracking distillate oil and a second catalytic cracking distillate oil, wherein the initial boiling point of the first catalytic cracking distillate oil is more than 20° C., the final boiling point of the second catalytic cracking distillate oil is less than 550° C., and the cut point between the first catalytic cracking distillate oil and the second catalytic cracking distillate oil is within a range of 140° C. and 250° C.;
   4) Carrying out a second separation on the first catalytic cracking distillate oil to obtain an olefin-rich stream having a C5+ olefin content of at least 50 wt %;
   5) Recycling at least a part of the olefin-rich stream to step 2) for further reaction; and
   6) Recycling at least a part of the butylene separated in step 3) to the fluidized catalytic conversion reactor upstream of the position at which the heavy feedstock oil is introduced to contact with the catalytic conversion catalyst for reaction under third catalytic conversion conditions, wherein the first catalytic conversion conditions include:
a reaction temperature of 500-800° C.;
a reaction pressure of 0.05-1 MPa;
a reaction time of 0.01-100 seconds;
a weight ratio of the catalytic conversion catalyst to the heavy feedstock oil of (1-200):1;
the second catalytic conversion conditions include:
a reaction temperature of 400-680° C.;
a reaction pressure of 0.05-1 MPa;
a reaction time of 0.01-100 seconds; and
a weight ratio of the catalytic conversion catalyst to the hydrocarbon oil feedstock of (1-100):1; and
the third catalytic conversion conditions include:
a reaction temperature of 650-800° C.;
a reaction pressure of 0.05-1 MPa;
a reaction time of 0.01 to 10 seconds; and a weight ratio of the catalytic conversion catalyst to the butylene of (20-200):1.

2. The method according to claim 1, further comprising the steps of:
2a) introducing an oxygen-containing organic compound into the second reaction zone of the fluidized catalytic conversion reactor to contact with the catalytic conversion catalyst therein for reaction under fourth catalytic conversion conditions including:
a reaction temperature of 300-550° C.,
a reaction pressure of 0.05-1 MPa,
a reaction time of 0.01-100 seconds, and
a weight ratio of the catalytic conversion catalyst to the oxygen-containing organic compound feedstock of (1-100):1.

3. The method according to claim 1, further comprising the step of:
7) Carrying out a hydrotreatment on the second catalytic cracking distillate oil to obtain a hydrogenated catalytic cracking distillate oil, recycling the hydrogenated catalytic cracking distillate oil to the first reaction zone of the fluidized catalytic conversion reactor for further reaction.

4. The method according to claim 1, further comprising the step of:
8) Regenerating the spent catalyst obtained by the separation in step 3) by coke burning to obtain a regenerated catalyst having a temperature of 650° C. or higher, and then recycling the regenerated catalyst to the upstream of the first reaction zone of the fluidized catalytic conversion reactor for use as the catalytic conversion catalyst.

5. The method according to claim 1, wherein the heavy feedstock oil used in step 1) is selected from the group consisting of petroleum hydrocarbons and mineral oils; the petroleum hydrocarbon is selected from vacuum gas oil, atmospheric gas oil, coking gas oil, deasphalted oil, vacuum residuum, atmospheric residuum, heavy aromatic raffinate, or combinations thereof; the mineral oil is selected from coal liquefaction oil, oil sand oil, shale oil, and a combination thereof; and
the hydrocarbon oil feedstock used in step 2) has an olefin content of 80 wt % or more.

6. The method according to claim 1, wherein:
the second separating of step 4) further comprises splitting the olefin-rich stream into a first olefin-rich stream having a lower boiling point and a second olefin-rich stream having a higher boiling point; the cut point between the first stream and the second stream is in a range of 140-200° C.; and
the step 5) further comprises introducing the first olefin-rich stream into the second reaction zone of the fluidized catalytic conversion reactor for further reaction, and introducing the second olefin-rich stream into a third reaction zone of the fluidized catalytic conversion reactor downstream of the second reaction zone for further reaction.

7. The method according to claim 1, wherein the fluidized catalytic conversion reactor is selected from a riser reactor, a fluidized bed reactor, an ascending transfer line, a descending transfer line, and a combination of two or more thereof.

8. The method according to claim 1, wherein the catalytic conversion catalyst comprises 1-50 wt % of a molecular sieve, 5-99 wt % of an inorganic oxide, and 0-70 wt % of a clay, based on the weight of the catalytic conversion catalyst;
the molecular sieve comprises at least one of a macroporous molecular sieve, a mesoporous molecular sieve and a microporous molecular sieve; and
the catalytic conversion catalyst further comprises 0.1 to 3 wt % of an active metal, based on the weight of the catalytic conversion catalyst; the active metal is at least one selected from the group consisting of Group VIII metals, Group IVA metals and rare earth metals.

9. The method according to claim 2, wherein the oxygen-containing organic compound is fed into the second reaction zone of the fluidized catalytic conversion reactor after being mixed with the hydrocarbon oil feedstock or the oxygen-containing organic compound is fed into the second reaction zone of the fluidized catalytic conversion reactor downstream of the position at which the hydrocarbon oil feedstock is introduced.

10. The method according to claim 1, wherein:
the first catalytic conversion conditions include:
a reaction temperature of 510-780° C.;
a reaction pressure of 0.1-0.8 MPa;
a reaction time of 0.1-80 seconds; and
a weight ratio of the catalytic conversion catalyst to the heavy feedstock oil of (3-180):1;
the second catalytic conversion conditions include:
a reaction temperature of 450-650° C.;
a reaction pressure of 0.1-0.8 MPa;
a reaction time of 0.1-80 seconds; and
a weight ratio of the catalytic conversion catalyst to the hydrocarbon oil feedstock of (3-70):1; and
the third catalytic conversion conditions include:
a reaction temperature of 680-780° C.;
a reaction pressure of 0.1-0.8 MPa;
a reaction time of 0.05 to 8 seconds; and
a weight ratio of the catalytic conversion catalyst to the butylene of (30-180):1.

11. The method according to claim 2, wherein the fourth catalytic conversion conditions including:
a reaction temperature of 400-530° C.,
a reaction pressure of 0.1-0.8 MPa,
a reaction time of 0.1-80 seconds, and
a weight ratio of the catalytic conversion catalyst to the oxygen-containing organic compound feedstock of (3-80):1.

12. The method according to claim 11, wherein the oxygen-containing organic compound comprises at least one of methanol, ethanol, dimethyl ether, methyl ethyl ether and ethyl ether.

13. The method according to claim 3, wherein the hydrotreatment conditions include: a hydrogen partial pressure of 3.0-20.0 MPa, a reaction temperature of 300-450° C., a hydrogen-to-oil volume ratio of 300-2000, and a volume space velocity of 0.1-3.0 h$^{-1}$.

14. The method according to claim 5, wherein the hydrocarbon oil feedstock used in step 2) has an olefin content of 90 wt % or more.

15. The method according to claim 5, wherein the hydrocarbon oil feedstock is a pure olefin feedstock.

16. The method according to claim 14, wherein the olefins in the hydrocarbon oil feedstock are derived from a C4+ fraction produced by dehydrogenation of an alkane feedstock, a C4+ fraction produced by a catalytic cracking unit in an oil refinery, a C4+ fraction produced by a steam cracking unit in an ethylene plant, a C4+ olefin-rich byproduct fraction of an MTO process, and a C4+ olefin-rich byproduct fraction of an MTP process.

17. The method according to claim 7, wherein the fluidized catalytic conversion reactor is a riser reactor.

18. The method according to claim 7, wherein the fluidized catalytic conversion reactor is a diameter-transformed riser reactor.

\* \* \* \* \*